(12) United States Patent
Kim et al.

(10) Patent No.: US 11,655,306 B2
(45) Date of Patent: May 23, 2023

(54) NK CELL-ACTIVATING FUSION PROTEIN, NK CELL, AND PHARMACEUTICAL COMPOSITION INCLUDING SAME

(71) Applicant: KOREA RESEARCH INSTITUTE OF BIOSCIENCE AND BIOTECHNOLOGY, Daejeon (KR)

(72) Inventors: Seok Ho Kim, Daejeon (KR); Jaemin Lee, Daejeon (KR); Duck Cho, Seoul (KR)

(73) Assignee: Korea Research Institute of Bioscience and Biotechnology

( * ) Notice: Subject to any disclaimer, the term of this patent is extended or adjusted under 35 U.S.C. 154(b) by 249 days.

(21) Appl. No.: 16/500,051

(22) PCT Filed: Apr. 5, 2018

(86) PCT No.: PCT/KR2018/004043
§ 371 (c)(1),
(2) Date: Oct. 1, 2019

(87) PCT Pub. No.: WO2018/186706
PCT Pub. Date: Oct. 11, 2018

(65) Prior Publication Data
US 2020/0148786 A1    May 14, 2020

(30) Foreign Application Priority Data
Apr. 5, 2017 (KR) .......................... 10-2017-0043988

(51) Int. Cl.
| | | |
|---|---|---|
| *C07K 16/32* | (2006.01) | |
| *A61P 35/00* | (2006.01) | |
| *A61K 9/00* | (2006.01) | |
| *C07K 14/52* | (2006.01) | |
| *C07K 16/28* | (2006.01) | |
| *A61K 39/00* | (2006.01) | |

(52) U.S. Cl.
CPC ............ *C07K 16/32* (2013.01); *A61K 9/0019* (2013.01); *A61P 35/00* (2018.01); *C07K 14/521* (2013.01); *C07K 16/2827* (2013.01); *A61K 2039/505* (2013.01); *C07K 2317/622* (2013.01); *C07K 2317/732* (2013.01); *C07K 2319/30* (2013.01)

(58) Field of Classification Search
CPC .................. C07K 16/32; C07K 14/521; C07K 16/2827; A61K 9/0019
See application file for complete search history.

(56) References Cited

U.S. PATENT DOCUMENTS

| 2010/0183516 A1 | 7/2010 | Ribbert et al. | |
| 2011/0059107 A1 * | 3/2011 | Allison | ................... A61P 29/00 530/387.9 |

FOREIGN PATENT DOCUMENTS

| EA | 19344 | 3/2014 | |
| JP | 2014518632 | 8/2014 | |
| KR | 10-2006-0079180 | 7/2006 | |
| KR | 10-2015-0063145 | 6/2015 | |
| KR | 10-1732126 | 5/2017 | |
| WO | WO2007097812 | 8/2007 | |
| WO | WO2009066820 | 5/2009 | |
| WO | WO2009114110 | 9/2009 | |
| WO | WO2012166588 | 12/2012 | |
| WO | WO2014043523 | 3/2014 | |
| WO | WO2016176756 | 11/2016 | |
| WO | WO-2016176756 A1 * | 11/2016 | ........... A61K 39/395 |
| WO | WO2017064222 | 4/2017 | |

OTHER PUBLICATIONS

Chen et al., "Fusion protein linkers: Property, design and functionality", Advanced Drug Delivery Reviews, 2013, 65(10):1357-1369.
Maeda et al., "Engineering of functional Chimeric Protein G-VargulaLuciferase", Analytical Biochemistry, 1997, 249(2):147-152.
Orlando., "Modification of proteins and low molecular weight substances with hydroxethyl starch (HES)", Inaugur Aldissertations, Giesen, 2003, 166:15.
Russion Office Action in RU Appln. No. 2019135054/10(069237), dated Jun. 1, 2020, 15 pages with English translation.
Australian Examination Report No. 1 in AU Appln. No. 2018248672, dated Sep. 22, 2020, 8 pages.
Cho et al., "CXCL16 signaling mediated macrophage effects on tumor invasion of papillary thyroid carcinoma", Endocrine-Related Cancer, 2016, 23(2):113-124.
Extended European Search Report in EP Appln. No. 18781754.9, dated Nov. 9, 2020, 9 pages.
Fang et al., "Chemokine CXCL16 expression suppresses migration and invasiveness and induces apoptosis in breast cancer cells", Mediators of Inflammation, 2014, 10 pages.
Gillies et al., "A new platform for constructing antibody-cytokine fusion proteins (immunocytokines) with improved biological properties and adaptable cytokine activity", Protein Engineering, Design and Selection, Oct. 2013, 26(1):561-569.
Kee et al., "CXCL16 suppresses liver metastasis of colorectal cancer by promoting TNF-a-induced apoptosis by tumor-associated macrophages" BMC Cancer, 2014, 14(1):949.
Lee et al., "An antibody designed to improve adoptive NK-Cell therapy inhibits pancreatic cancer progression in a murine model", Cancer Immunology Research, 12 pages.

(Continued)

*Primary Examiner* — Peter J Reddig
*Assistant Examiner* — Cheng Lu
(74) *Attorney, Agent, or Firm* — Fish & Richardson P.C.

(57) ABSTRACT

A fusion protein for cancer treatment and a use thereof is disclosed. The fusion protein for preventing or treating cancer of the present invention includes a fusion polypeptide including: an antibody or fragment thereof binding to a tumor-associated antigen; a linker; and a NK cell-inducing protein of CXCL16, wherein a co-administration of the fusion polypeptide along with the NK cells, an immunocyte therapeutic agent, greatly increases an influx of the NK cells into cancer expressing a certain antigen, thereby having a remarkable effect on preventing or treating cancer.

13 Claims, 21 Drawing Sheets
Specification includes a Sequence Listing.

(56) References Cited

OTHER PUBLICATIONS

Lu et al., "CXCL16 functions as a novel chemotactic factor for prostate cancer cells in vitro", Molecular Cancer Research, 2008, 6(4):546-554.

Ludwig et al., "Enhanced expression and shedding of the transmembrane chemokine CXCL16 by reactive astrocytes and glioma cells", Journal of Neurochemistry, 2005, 93(5):1293-1303.

Yoon et al., "Irradiation of breast cancer cells enhances CXCL16 ligand expression and induces the migration of natural killer cells expressing the CXCR6 receptor", Cytotherapy, 2016, 18(12):1532-1542.

Zhang et al., "MiR-451 inhibits cell growth and invasion by targeting CXCL16 and is associated with prognosis of osteosarcoma patients", Tumor Biology, 2015, 36(3):2041-2048.

Beziat et al., "CD56brightCD16+ NK Cells: A Functional Intermediate Stage of NK Cell Differentiation", The Journal of Immunology, May 2011, 186:6753-6761.

Hess et al., "Evaluation of antibody-chemokine fusion proteins for tumor-targeting applications", Experimental Biology and Medicine, 2014, 239:842-852.

International Search Report and Written Opinion in International Application No. PCT/KR2018/004043, dated Jul. 18, 2018, 12 pages with English Translation.

Duckert et al., "Prediction of proprotein convertase cleavage sites", Protein Engineering, Design & Selection, 2004, 17(1):107-112.

Gerbino, "The Science and Practice of Pharmacy, 21st Edition", American Journal of Pharmaceutical Education, 2006, 70(3):71.

\* cited by examiner

IgG  Mesothelin-FC  fusion polypeptide

Control IgG

Non-cleavable fusion polypeptide fusion polypeptide

NK CELL-ACTIVATING FUSION PROTEIN, NK CELL, AND PHARMACEUTICAL COMPOSITION INCLUDING SAME

SEQUENCE LISTING

The instant application contains a Sequence Listing which has been submitted electronically in ASCII format and is hereby incorporated by reference in its entirety. Said ASCII copy, created on Dec. 30, 2019, is named 49183 0002US1 ST25.txt and is 51,550 bytes in size.

TECHNICAL FIELD

The present invention relates to a novel anti-cancer immune cell therapy using a fusion protein and natural killer cells in order to increase an influx of the natural killer cells into cancer and maximize an antibody-dependent cellular cytotoxicity (ADCC).

Also, the present invention relates to a method for treating cancer with the fusion protein as well as various uses of the fusion protein.

BACKGROUND

A natural killer (NK) cell is an effector cell working in a first line of a defense mechanism of an immune system in vivo, such as performing a function of removing tumor cells and host cells infected with bacteria, intracellular parasites or viruses without prior sensitization with antigens; rejecting an inappropriate bone-marrow transplantation; regulating an immune response of T cells; and the like.

An immunological function of the NK cell depends on a balance between a stimulatory signal for inducing a killing function thereof and an inhibitory signal for inhibiting the killing function. Particularly, the NK cell, which strongly receives the stimulatory signal, attacks and removes a target cell, and the NK cell, which strongly receives the inhibitory signal, leaves the target cell alive.

As the killing function of the NK cell, there are antibody-dependent cellular cytotoxicity (ADCC) and natural killing. The ADCC and the natural killing have it in common that both need an activation of protein tyrosine kinase (PTK) and are blocked by means of the inhibitory signal delivered by an inhibitory receptor of the NK cell. The killing function of the NK cell depends on the balance between the stimulatory signal and the inhibitory signal, and thus the NK cell may distinguish normal host cells from infected or cancerized cells to remove the latter.

The NK cell may be classified according to an expression level of CD56, and at least 90% of $CD56^{dim}$ NK cells are distributed in peripheral blood NK cells. It is known that the $CD56^{dim}$ has higher cytotoxicity than other CD56-expressing NK cells and shows a high expression of killer Ig-like receptors (KIR) and perforin, which are activating receptors of the NK cell. It is also known that $CD56^{bright}$ NK cells are smaller in number and have lower cytotoxic capacity than the $CD56^{dim}$ NK cells. However, it is reported that the $CD56^{bright}$ NK cells have not only a high immunoregulatory function (IFN-gamma, TNF-alpha, etc.), but also a high ADCC function (*The Journal of Immunology*, 2011, 186: 6753-6761). In particular, the $CD56^{bright}$ NK cells are expected to have an improved effect in combination therapy on antibody and cancer.

On the other hand, it is well known that a tumor may express a unique protein associated with a malignant phenotype thereof or may over-express a certain protein more in number than normal cells. The expression of the unique protein on a surface of a tumor cell makes it possible to probe the tumor for its phenotypic identity and biochemical composition and activity, thus providing an opportunity for diagnosing and characterizing a disease, or also possible to target a tumor-associated antigen, thus developing a novel therapeutic method for the tumor.

It is known that an antibody showing an antigen-antibody reaction specific to the tumor-associated antigen attacks cancer cells and causes cell deaths by inducing various in vivo immune responses (antibody-dependent cellular cytotoxicity (ADCC) activity, complement-dependent cellular cytotoxicity (CDC) activity, etc.). Thus, the antibody useful in tumor treatment, etc. is being developed now, but little research and development has been done to enhance a therapeutic efficacy thereof.

Against these backdrops, there is a need to perform research and development on a method for effectively treating cancer by using NK cells and cancer antigens, which are specifically expressed on the surface of cancer cells.

PRIOR ART REFERENCES

Patent Documents

Korean Patent Publication No. 10-2006-0079180
Korean Patent Publication No. 10-2015-0063145

DETAILED DESCRIPTION OF THE INVENTION

Technical Problem

The present invention provides a fusion polypeptide comprising:
an antibody or fragment thereof binding to a tumor-associated antigen;
a linker; and
a natural killer (NK) cell-inducing protein of CXCL16.

The present invention also provides a nucleic acid coding the fusion polypeptide; a vector comprising the same; or a host cell comprising the vector.

The present invention also provides a pharmaceutical composition for preventing or treating cancer, comprising a fusion polypeptide comprising:
an antibody or fragment thereof binding to a tumor-associated antigen;
a linker; and
a NK cell-inducing protein of CXCL16.

The present invention also provides a pharmaceutical composition for preventing or treating cancer, comprising a fusion polypeptide comprising:
an antibody or fragment thereof binding to a tumor-associated antigen;
a linker; and
a NK cell-inducing protein of CXCL16,
and a NK cells.

The present invention also provides a composition comprising the fusion polypeptide to be used in cancer treatment.

The present invention also provides a use of the fusion polypeptide in preparing a drug for cancer treatment.

The present invention also provides a use of the fusion polypeptide for cancer treatment.

The present invention also provides a method for treating cancer, by administering the composition comprising the fusion polypeptide into a patient in a pharmaceutically effective amount.

Technical Solution

The present inventors have performed research and development on a method for effectively introducing a natural killer (NK) cell, an immunocyte therapeutic agent, into a cancer tissue. As a result, the present inventors have identified that, out of receptors of an activity-inducing substance expressed on a surface of the NK cell, $CXCR_3$ and CXCR6 are over-expressed on the surface of the NK cell, then identified that, out of ligands thereof, CXCL16 is effective in a migration of the NK cell, and then identified that an induction of the NK cell into cancer is remarkably increased and thus has a remarkable effect on cancer treatment by preparing and administering a fusion protein specific to a tumor-associated antigen as well as CXCL16 having an NK cell-inducing property, thereby completing the present invention.

As used herein, the term "tumor-associated antigen" means an antigen, which is not expressed on a normal cell or over-expressed only on a tumor cell contrary to the normal cell, preferably specifically expressed on a surface of the tumor cell, wherein such antigen refers to an antigenic substance produced from tumor cells.

The tumor-associated antigen, which is specifically expressed on a tumor, may include, for example, 4-1BB (CD137), 5T4, $AGS_{-5}$, AGS-16, Angiopoietin 2, CD19 (Cluster of Differentiation 19), B7.1 (CD80), B7.2 (CD86), B7DC, B7H1, B7H2, B7H3, BT-062, BTLA, CAIX, Carcinoembryonic antigen, CTLA4, Cripto, ED-B, ErbB1, ErbB2, ErbB3, ErbB4, EGFL7, EpCAM, EphA2, EphA3, EphB2, FAP, fibronectin, folate receptor, Ganglioside GM3, GD2, glucocorticoid-induced tumor necrosis factor receptor (GITR), gplOO, gpA33, GPNMB, ICOS, IGFIR, integrin αυ, Integrin αυβ, KIR, $LAG_{-3}$, Lewis Y, Mesothelin, c-MET, Her2 (human EGFR-related 2), MN carbonic anhydrase IX, MUC1, MUC16, $Nectin_{-4}$, NKGD2, NOTCH, OX40, OX40L, PD-1, PD-L1 (programmed death-ligand 1), PSCA, PSMA, RANKL, ROR1, ROR2, SLC44A4, Syndecan-1, TACI, TAG-72, Tenascin, TIM3, TRAILR1, TRAILR2, EGFR, VEGFR-1, VEGFR-2, $VEGFR_{-3}$ or the like, but not limited thereto. In one Example of the present invention, an effect of a fusion polypeptide was identified on mesothelin, PD-L1, Her2, CD19, MUC1, EGFR and VEGFR.

As used herein, the term "antibody" includes a whole antibody, an antibody fragment holding an antigen-recognizing and -binding capacity, a monoclonal antibody, a polyclonal antibody, and an antibody-like substance. The antibody may be IgM, IgG (for example, IgG1, IgG2, IgG3 or IgG4), IgD, IgA, or IgE.

As used herein, the term "antibody fragment" means a portion of the whole antibody, generally a molecule comprising an antigen-binding or variable region of the whole antibody. An example of the antibody fragment includes Fab, Fab', F(ab')2, and Fv fragment; and a single domain antibody.

The "antibody or fragment thereof" may specifically or preferably bind to a tumor cell compared to a non-tumor cell or a normal cell, preferably a tumor-associated antigen specifically expressed in the tumor. Herein, "specifically bind" or "preferably bind" means that a binding between two binding partners (e.g., an antibody and a binding partner thereof, i.e., an antigen) is selective with regard to the two binding partners and may be distinguished from undesired or non-specific interactions.

As used herein, the term "single-chain Fv" or "scFv (single-chain variable fragment)" refers to an antibody, in which heavy chain and light chain variable domains of a conventional two-chain antibody bind to each other to form one chain. Typically, a linker peptide is inserted between the two chains to allow an appropriate folding and a formation of an active binding site.

As used herein, the term "antibody binding to an antigen" refers to an antibody useful as a therapeutic agent, in which the antibody targets an antigen by binding to the antigen with sufficient affinity.

As used herein, the term "linker" means a peptide, which connects a first molecule (e.g., an antibody or fragment thereof binding to a tumor-associated antigen) to a second molecule (an NK cell-inducing protein of CXCL16) through a chemical bonding, etc.

As used herein, the term "cancer" or "tumor" means a pathological condition in humans, characterized by an uncontrolled cell proliferation. The cancer or tumor includes a carcinoma, lymphoma, blastoma and leukemia, but not limited thereto. More specific non-limiting examples of cancers include a lung cancer (small cell and non-small cell), breast cancer, prostate cancer, carcinoid, bladder cancer, gastric cancer, pancreatic cancer, liver cancer (hepatocellular), hepatoblastoma, colon cancer, head and neck squamous cell carcinoma (HNSCC), esophagus cancer, ovarian cancer, cervical cancer, solenoma, mesothelioma, melanoma, sarcoma, osteosarcoma, liposarcoma, thyroid cancer, desmoma, acute myelogenous leukemia (AML), and chronic myelogenous leukemia (CML).

As used herein, the term "expression vector" includes a nucleotide sequence coding a molecule of interest, which is agonistically bound to a promoter.

As used herein, the terms "polypeptide," "peptide" and "protein" are interchangeably used and include a reference to a polymer of amino acid residues. The terms are applied not only to natural amino acid polymers, but also to artificial amino acid polymers, which are chemical analogues of natural amino acids, to which at least one amino acid residue corresponds. The terms are also applied to the polymers containing a conservative amino acid replacement such that protein may remain agonistic.

As used herein, the term "host cell" means a cell capable of supporting a replication or expression of the expression vector. The host cell may be prokaryotic cells, for example, *Escherichia coli*, or eucaryotic cells, for example, yeast, insect, amphibian or mammalian cells.

With regard to a growth or progression of tumor or cancer, the terms "inhibiting," "reducing" and "decreasing" refer to inhibiting a growth, diffusion or metastasis of a patient's tumor or cancer by up to a measurable amount by using any method known in the art. The growth, progression or diffusion of the tumor or cancer is inhibited, reduced or decreased, if a size of the tumor is reduced by at least about 10%, 20%, 30%, 50%, 80% or 100% compared to the tumor size measured, for example, before co-administering a fusion polypeptide of the present invention and NK cells, an immunocyte therapeutic agent, or before administering the fusion polypeptide.

The present invention provides a fusion polypeptide comprising: an antibody or fragment thereof binding to a tumor-associated antigen; a linker; and a NK cell-inducing protein of CXCL16.

The fusion polypeptide according to the present invention may specifically bind to a cell surface of a tumor by comprising an antibody or fragment thereof binding to a tumor-associated antigen, and may also induce the NK cell into a targeted tumor cell by means of CXCL16, i.e., a NK cell-inducing protein, which is cleaved and released after an antigen-antibody binding.

The fusion polypeptide according to the present invention binds to a tumor-targeting surface antigen by comprising an antibody or fragment thereof specifically binding to a tumor-associated antigen. The tumor-targeting surface antigen is widely known in the art, and may be, for example, mesothelin, PD-L1, Her2, CD19, MUC1, EGFR, VEGFR, B7H1, B7H2, B7H3, BT-062, BTLA, CAIX, 4-1BB, 5T4, AGS-5 or AGS-16, but not limited thereto.

The antibody or fragment thereof specifically binding to the tumor-associated antigen includes a single-chain Fv (scFv), Fab, Fab', F(ab')2, disulfide-stabilized antibody, etc., and particularly may be the single-chain Fv (scFv).

The antibody or fragment thereof specifically binding to the tumor-associated antigen may be prepared according to a preparation method known in the art.

In an exemplary embodiment according to the present invention, the antibody is the single-chain Fv (scFv). $V_H$ and $V_L$ regions of the scFv antibody contain a single chain, which is folded to form an antigen-binding site similar to the one, which is found in a two-chain antibody. Once folded, the single-chain antibody is stabilized by means of a non-covalent interaction. In a more specific exemplary embodiment, the scFv is formed by means of recombination. A conservative variant of the antibody of the present invention may be conventionally prepared, and the conservative variant used in the scFv fragment will maintain an important amino acid residue, which is needed for a precise folding and stabilization between the $V_H$ and $V_L$ regions.

According to one exemplary embodiment of the present invention, scFv is mesothelin scFv, which has an amino acid sequence represented by SEQ ID NO: 1, and particularly may be coded by means of a base sequence represented by SEQ ID NO: 2.

According to other exemplary embodiment of the present invention, scFv is PD-L1 scFv, which may comprise a heavy chain ($V_H$) of an amino acid sequence represented by SEQ ID NO: 3, particularly coded by means of a base sequence represented by SEQ ID NO: 4; and a light chain ($V_L$) of an amino acid sequence represented by SEQ ID NO: 5, particularly coded by means of a base sequence represented by SEQ ID NO: 6, and the tumor-associated antigen, i.e. PD-L1 may be the one coded by means of a base sequence represented by SEQ ID NO: 7, but not limited thereto.

According to another exemplary embodiment of the present invention, scFv is Her2 scFv, which may comprise a heavy chain of an amino acid sequence represented by SEQ ID NO: 8, particularly coded by means of a base sequence represented by SEQ ID NO: 9; and a light chain of an amino acid sequence represented by SEQ ID NO: 10, particularly coded by means of a base sequence represented by SEQ ID NO: 11, and the tumor-associated antigen, i.e. Her2 may be the one coded by means of a base sequence represented by SEQ ID NO: 12, but not limited thereto.

According to another exemplary embodiment of the present invention, scFv is CD19 scFv, which may comprise a heavy chain of an amino acid sequence represented by SEQ ID NO: 28, particularly coded by means of a base sequence represented by SEQ ID NO: 29; and a light chain of an amino acid sequence represented by SEQ ID NO: 30, particularly coded by means of a base sequence represented by SEQ ID NO: 31, but not limited thereto.

According to another exemplary embodiment of the present invention, scFv is MUC-1 scFv, which may comprise a heavy chain of an amino acid sequence represented by SEQ ID NO: 32, particularly coded by means of a base sequence represented by SEQ ID NO: 33; and a light chain of an amino acid sequence represented by SEQ ID NO: 34, particularly coded by means of a base sequence represented by SEQ ID NO: 35, but not limited thereto.

According to another exemplary embodiment of the present invention, scFv is EGFR scFv, which may comprise a heavy chain of an amino acid sequence represented by SEQ ID NO: 36, particularly coded by means of a base sequence represented by SEQ ID NO: 37; and a light chain of an amino acid sequence represented by SEQ ID NO: 38, particularly coded by means of a base sequence represented by SEQ ID NO: 39, but not limited thereto.

According to another exemplary embodiment of the present invention, scFv is VEGFR scFv, which may comprise a heavy chain of an amino acid sequence represented by SEQ ID NO: 40, particularly coded by means of a base sequence represented by SEQ ID NO: 41; and a light chain of an amino acid sequence represented by SEQ ID NO: 42, particularly coded by means of a base sequence represented by SEQ ID NO: 43, but not limited thereto.

The scFv antibody may be directly bound to a peptide linker through a light chain, and may be bound thereto through an Fc region, to which scFv is bound.

According to one exemplary embodiment of the present invention, Fc (constant region) may have an amino acid sequence of SEQ ID NO: 13, and particularly may be coded by means of a base sequence represented by SEQ ID NO: 14, but not limited thereto.

A linker according to the present invention will not have a certain biologic activity except binding the regions as a peptide linker or conserving some minimum distance or other spatial relationship between the regions, but constituent amino acids may be selected to have an influence on some properties of the molecules, for example, folding, net charge or hydrophobicity. Also, the linker may comprise a cleavage sequence such that CXCL16 may be isolated after an antibody binds to a tumor-associated antigen. An antibody or fragment thereof specifically binding to a tumor-associated antigen may be linked through a peptide linker having a length of at most 50 amino acids, generally at most 40 amino acids, preferably at most 30 amino acids, more preferably at most 20 amino acids, and much more preferably 1 to 10 amino acids.

For example, the peptide linker may comprise a sequence, which is cleaved by any protease, and particularly may be the peptide linker comprising consecutive amino acid residues of RVKR, which is cleaved by furin, but not limited thereto.

According to one exemplary embodiment of the present invention, a fusion polypeptide according to the present invention comprises a furin cleavage site, which is cleaved by furin, that is, the furin cleavage site comprising consecutive amino acid residues, which may be cleaved by furin, such that an NK cell-inducing protein may be released from a cancer cell.

The furin cleavage site may be any polypeptide site, which may be cleavable by means of furin. As reported by Duckert, etc. (Document [Duckert et al., Protein Engineering, Design & Selection 17(1):107-112 (2004)], which is herein incorporated by reference in its entirety), furin is an enzyme "based on an evolutionarily conserved dibasic- and monobasic-specific $CA^{2+}$-dependent serine protease, also called subtilisin/kexin-like proprotein convertases."

A sequence of the furin cleavage site, which is known in the document, etc., is incorporated herein, and particularly has an amino acid sequence of SEQ ID NO: 15 and may be coded by means of a base sequence represented by SEQ ID NO: 16, but not limited thereto.

The antibody or fragment thereof binding to a tumor-associated antigen may be bound to the furin cleavage sequence through an amino terminus of the furin cleavage site, and may be directly bound to the light chain, heavy chain, Fc (constant region) or framework regions of the antibody.

The fusion protein of the present invention comprises a NK cell-inducing protein of CXCL16, such that the inventive fusion protein may induce the NK cell into a tumor cell having the antibody bound to the tumor-associated antigen.

The "NK cell-inducing protein" according to the present invention means a protein for inducing the NK cell into the tumor cell, that is, CXCL16, which is the protein capable of migrating the NK cell into the cancer cell by means of chemokine.

Particularly, the CXCL16 may have an amino acid sequence of SEQ ID NO: 17. The CXCL16 may be coded by means of a base sequence of SEQ ID NO: 18.

The NK cell-inducing protein may be linked to the antibody or fragment thereof through the peptide linker. The linker according to the present invention will not have a certain biologic activity except binding the regions as a peptide linker or conserving some minimum distance or other spatial relationship between the regions, but constituent amino acids may be selected to have an influence on some properties of the molecules, for example, folding, net charge or hydrophobicity. Also, the linker may comprise a cleavage sequence, e.g. the cleavage sequence by means of any protease such that CXCL16 may be isolated after an antibody binds to a tumor-associated antigen.

According to one exemplary embodiment of the present invention, the peptide linker comprises a furin cleavage site, which is cleaved by furin, that is, the furin cleavage site comprising consecutive amino acid residues, which may be cleaved by furin.

The fusion polypeptide according to the present invention may be prepared by means of a non-recombination method or a recombination method known in the art, preferably by means of the recombination method.

In other words, an expression vector may be prepared by inserting cDNA coding the antibody or fragment thereof binding to a tumor-associated antigen; a linker; and a NK cell-inducing protein of CXCL16 into the vector.

According to one exemplary embodiment of the present invention, the expression vector is prepared by inserting a base sequence comprising mesothelin scFv and Fc into a vector, particularly, a pcDNA3.1 vector, and by inserting a furin cleavage site and a base sequence coding the NK cell-inducing protein behind an immunoglobulin sequence. An example of the prepared expression vector is as described in a following FIG. 2.

The prepared expression vector may be expressed in bacterial, plant, yeast, insect and mammalian cells. Those skilled in the art may prepare the fusion polypeptide by using a number of expression systems, which may be used in a protein expression, including *Escherichia coli*, other bacterial host, yeast and various higher eucaryotic cells, for example, COS, CHO, HeLa and myeloma cell lines.

According to one exemplary embodiment of the present invention, the fusion polypeptide may be prepared by transfecting a CHO cell, from which furin is removed, with the expression vector.

The prepared fusion polypeptide may provide a targeted fusion polypeptide by being purified according to a standard process in the art including ammonium sulfate precipitation, affinity column, column chromatography, etc.

The present invention provides a nucleic acid coding the fusion polypeptide.

The present invention provides an expression vector comprising a nucleic acid sequence coding the fusion polypeptide. Particularly, the present vector may provide the expression vector having a structure as shown in FIG. 2, which may have a base sequence of SEQ ID NO: 19.

The present invention provides a host cell comprising the expression vector. Particularly, such host cell may be one cell selected from COS, CHO, HeLa and myeloma cell lines, but not limited thereto.

The present invention provides a pharmaceutical composition for preventing or treating cancer, comprising a fusion polypeptide having: an antibody or fragment thereof binding to a tumor-associated antigen; a linker; and a NK cell-inducing protein of CXCL16.

The pharmaceutical composition for preventing or treating cancer according to the present invention is an immunocyte therapeutic agent, particularly wherein such composition has a remarkable effect on preventing or treating cancer through an induction of the NK cells into cancer. The pharmaceutical composition for preventing or treating cancer according to the present invention includes not only a direct therapeutic effect but also an action as an anti-cancer adjuvant.

According to one exemplary embodiment of the present invention, it was identified that a distribution of cells is changed from $CD56^{dim}$ into $CD56^{bright}$ with regard to the NK cells by means of CXCL16 of the fusion polypeptide prepared according to the present invention, and also identified that the pharmaceutical composition of the present invention is effective in preventing or treating cancer by means of a differentiation into $CD56^{bright}$ having a higher ADCC effect compared to $CD56^{dim}$.

The present invention also provides a pharmaceutical composition for preventing or treating cancer, comprising a fusion polypeptide having: an antibody or fragment thereof binding to a tumor-associated antigen; a linker; and a NK cell-inducing protein of CXCL16, and the NK cells.

According to the present invention, a co-administration of the fusion polypeptide along with the NK cells, an immunocyte therapeutic agent, greatly increases an influx of the NK cells into cancer, thereby having a remarkable effect on preventing or treating cancer.

The pharmaceutical composition to be used in the present invention may be formulated into a dosage form by means of a standard technique, using at least one physiologically acceptable carrier or excipient. A suitable pharmaceutical carrier is disclosed in the present invention and the document (Remington: The Science and Practice of Pharmacy, 21st Ed., University of the Sciences in Philadelphia, Lippencott Williams & Wilkins (2005)).

Such pharmaceutical composition may be formulated into a dosage form such that the inventive fusion polypeptide and/or the NK cells may be administered via any suitable route, for example, an inhalation, local, nasal, oral, parenteral or intrarectal route. Thus, the administration of the pharmaceutical composition mentioned above may be performed by means of an intradermal, subcutaneous, intravenous, intramuscular, intranasal, inhalational, intracerebral, endotracheal, intra-arterial, intraperitoneal, intravesical, intrapleural, intracoronary, subcutaneous or intratumoral injection, or by using a syringe or other devices. A percutaneous administration is also considered along with an inhalation or aerosol administration. A tablet and capsule may be administered orally, rectally or vaginally.

The pharmaceutical composition will comprise the fusion polypeptide, or the fusion polypeptide and NK cells, which are conventionally dissolved in a pharmaceutically acceptable carrier, preferably an aqueous carrier. The fusion polypeptide and NK cells may be provided together or separately. Various aqueous carriers, for example, buffered salt water, etc. may be used. Such solution has a bactericidal property and does not generally have an undesirable substance. Such composition may be sterilized by means of a conventional, widely known sterilization technique. The composition may contain a pharmaceutically acceptable adjuvant, as required to meet the physiological conditions, for example, a pH adjuster and buffer, toxicity adjusting agent, etc. for example, sodium acetate, sodium chloride, potassium chloride, calcium chloride, sodium lactate, etc. A concentration of the fusion polypeptide in such dosage form may be extensively various, and may be selected mainly based on a fluid volume, viscosity, weight, etc. according to a selected certain administration mode and a patient's need.

The pharmaceutical composition of the present invention is suitable for a parenteral administration, including an intravenous or intracoelomic administration.

The fusion polypeptide and/or NK cells of the present invention may be formulated into a dosage form for the parenteral administration via an injection, for example, a bolus or continuous injection. The dosage form for injection may be present along with an added preservative in a unit-dosage form container, for example, an ampule or a multi-dose container. An injectable composition is preferably an aqueous isotonic solution or suspension, and a suppository is preferably prepared from a lipid emulsion or suspension. The composition may be sterilized and/or contain an adjuvant, for example, a preservative, stabilizer, humectant or emulsifier, dissolution promoter, osmoregulatory salt and/or buffer. On the other hand, the active component may be present in a form of powder, which is made up before use by means of a suitable vehicle, for example, sterile pyrogen-free water. Also, the active component may contain other therapeutically valuable substances. The compositions are prepared according to a conventional mixing, granulation or coating method, respectively, and contain about 0.1 to 75%, preferably 1 to 50% of an active component.

In case of an oral administration, the pharmaceutical composition or drug may take on a form of tablet or capsule, which is prepared, for example, by conventional means, along with a pharmaceutically acceptable excipient. It is preferable that such pharmaceutical composition or drug should be the tablet and gelatin capsule, containing the active component, that is, the composition of the present invention along with: (a) a diluent or filler, for example, lactose, dextrose, sucrose, mannitol, sorbitol, cellulose (for example, ethyl cellulose, and microcrystalline cellulose), glycine, pectin, polyacrylate and/or calcium hydrogen phosphate, and calcium sulphate; (b) a lubricant, for example, silica, talcum, stearic acid, magnesium or calcium salt thereof, metallic stearate, colloidal silicon dioxide, hydrogenated vegetable oil, maize starch, sodium benzoate, sodium acetate and/or polyethylene glycol; also, in case of the tablet, (c) a binder, for example, magnesium aluminum silicate, starch paste, gelatin, tragacanth, methylcellulose, sodium carboxymethylcellulose, polyvinyl pyrrolidone and/or hydroxypropyl methylcellulose; in some cases, (d) a disintegrating agent, for example, starch (for example, potato starch or sodium starch), glycollate, agar, alginic acid or sodium salt thereof, or an effervescent blend; (e) a humectant, for example, sodium lauryl sulphate; and/or (f) an absorbent, coloring agent, flavoring agent and sweetening agent.

The present invention administers the pharmaceutical composition into a patient in a therapeutically effective dose for preventing, treating or inhibiting a disease such as cancer, or a malignant condition thereof. The pharmaceutical composition is administered into the patient in a sufficient amount enough to draw an effective therapeutic or diagnostic response from the patient. The effective therapeutic or diagnostic response refers to the response, which at least partially inhibits or delays symptoms or complications of the disease or malignant condition. A suitable amount for performing such administration is defined as a "therapeutically effective amount."

A dosage of the fusion polypeptide and/or NK cells to be administered varies depending on a mammal's species, weight, age, individual condition, surface area of a region to be treated, and administration type. A size of the dose may be also determined according to a presence, property and degree of any side effect to a certain patient, which accompanies an administration of a certain compound.

A unit dosage to be administered into a mammal of about 50 to 80 kg, preferably a human, may contain the fusion polypeptide in an amount of about 1 mg/kg to 5 mg/kg, and may contain the NK cells in an amount of about $1 \times 10^5$ cells/kg to $2 \times 10^7$ cells/kg.

Typically, the dosage of the composition of the present invention is a sufficient dosage enough to achieve a targeted effect. An optimal administration schedule may be determined by measuring the fusion polypeptide and/or NK cells and calculating an accumulation thereof in the patient's body. Such composition may be provided at least once a day, week, month or year. Those skilled in the art may easily determine an optimal dosage, administration method and repetition rate. Those skilled in the art may determine an optimal administration for administering the fusion polypeptide and/or NK cells into humans according to an established protocol known in the art and disclosed in the present invention. However, it is to be understood that an actual dosage of an effective component should be determined considering various related factors such as a disease to be treated, a severity of the disease, an administration route, a patient's weight, age, gender and the like, and thus the dosage is not construed to limit the scope of the present invention in any aspect.

The present invention also provides a composition comprising the fusion polypeptide to be used in cancer treatment.

The present invention also provides a use of the fusion polypeptide in preparing a drug for cancer treatment.

The present invention also provides a use of the fusion polypeptide for cancer treatment.

The present invention also provides a method for treating cancer, by administering the composition comprising the fusion polypeptide into a patient in a pharmaceutically effective amount. The therapeutic method of cancer may be performed by administering the NK cells together, thus showing an improved therapeutic effect accordingly.

Matters mentioned in the use, composition and therapeutic method of the present invention are equally applied, if not contradictory to each other.

Advantageous Effects

A fusion protein for preventing or treating cancer according to the present invention comprises a fusion polypeptide comprising: an antibody or fragment thereof binding to a tumor-associated antigen; a linker; and a NK cell-inducing protein of CXCL16, wherein a co-administration of the fusion polypeptide along with the NK cells, an immunocyte therapeutic agent, greatly increases an influx of the NK cells into cancer expressing a certain antigen, thereby having a remarkable effect on preventing or treating cancer.

BRIEF DESCRIPTION OF THE DRAWINGS

FIG. 26 is a graph of showing the induction of NK cells into a cancer tissue according to an administration of the fusion polypeptide prepared according to the present invention as well as the NK cells.

FIG. 27 is a graph of showing results of identifying a therapeutic effect by administering mesothelin scFv fusion polypeptide prepared according to the present invention into an animal model with transplanted pancreatic cancer along with the NK cells.

FIG. 28 is a graph of showing results of identifying a therapeutic effect by administering PD-L1 scFv fusion polypeptide prepared according to the present invention into an animal model with transplanted pancreatic cancer along with the NK cells.

FIG. 29 is a graph of showing results of identifying a therapeutic effect by administering Her2 scFv fusion polypeptide prepared according to the present invention into an animal model with transplanted pancreatic cancer along with the NK cells.

FIG. 30 is a graph of showing a change in distribution of NK cells upon treatment of the NK cells with CXCL16 and IL-2 for a short period of time.

FIG. 31 is a graph of showing a change in distribution of NK cells upon treatment of the NK cells with CXCL16 and IL-2 for a long period of time.

MODE FOR INVENTION

Hereinafter, the present invention will be described in detail through preferred Examples for better understanding of the present invention. However, the following Examples are provided only for the purpose of illustrating the present invention, and thus the present invention is not limited thereto.

<Example 1> Identification of Migration of Expanded Natural Killer Cells by Means of Chemokine In order to identify a degree of migration of expanded natural killer (NK) cells according to a chemokine type, the expanded NK cells were collected and centrifuged at 1,500 rpm. Then, supernatant was removed therefrom and washed with PBS, after which the number of cells was counted. As a chemokine, CXCL9, CXCL10, CXCL11 and CXCL16 were divided by 10 nM onto a bottom layer of a Boyden chamber plate, and the expanded NK cells were divided by $2 \times 10^5$ cells onto an upper layer of the Boyden chamber plate. After that, the resulting cells were cultured in a $CO_2$ incubator at 37° C. for two hours, after which the bottom layer was collected therefrom and centrifuged at 1,500 rpm. Then, a PBS washing was performed, after which a CD56-PE staining was carried out at 4° C. for 30 minutes and washed with PBS. For an FAC analysis, Count Bright Absolute Counting Beads (Invitrogen) were divided by 50 ul thereto, and the FACS analysis was performed.

Figure 1:
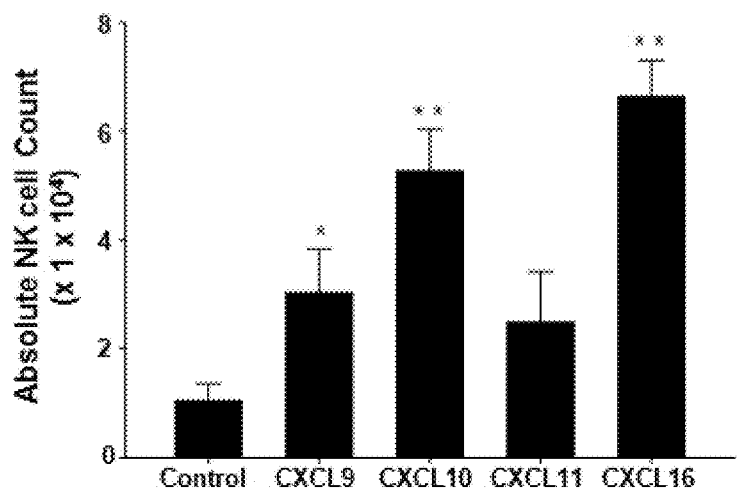
FIG. 1 is a graph of showing results of identifying a degree of migration of expanded natural killer (NK) cells according to a chemokine type.

The results thereof were shown in FIG. 1.

As identified in FIG. 1, it was identified that CXCL16 shows a remarkable effect on the migration of the expanded NK cells compared to other chemokine types.

<Example 2> Preparation and Purification of a Fusion Polypeptide [NK Cell Recruitment Protein (NRP)-Body]

Prepared was a recombinant vector, to which the followings were bound: a scFv sequence for recognizing a cancer-targeting antigen; a furin sequence for serving as a linker; and CXCL16 (NK cell Recruitment Protein; NRP) for inducing an influx of NK cells at the highest efficiency.

Figure 2:
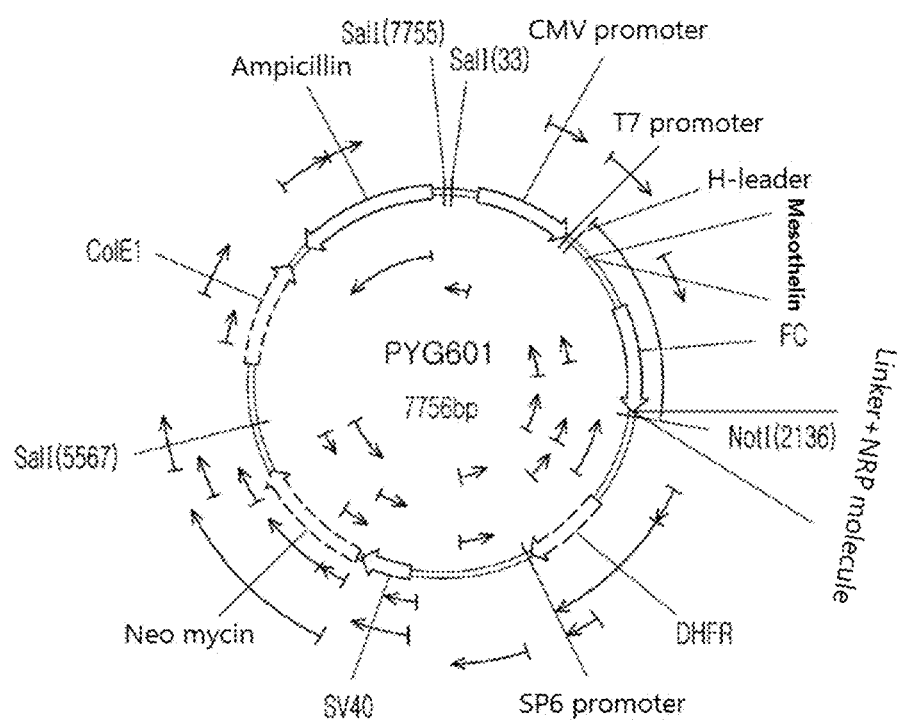
FIG. 2 is a schematic diagram of showing an expression vector for preparing a fusion polypeptide according to the present invention.

A structure of the particular recombinant vector, to which the scFv sequence for recognizing mesothelin as a target antigen was bound, was shown in FIG. 2.

A pcDNA3.1 vector was decomposed with a Sfi1 enzyme for two hours and purified to prepare a vector for ligation. To prepare mesothelin scFv, an amplification was performed through a PCR based on a primer sequence as shown in a following table 1 to obtain a mesothelin scFv base sequence of SEQ ID NO: 2, after which the vector, an insertion sample and T4 ligase were mixed together, and cultured at 25° C. for two hours to perform a ligation between the vector and the insertion. A resulting product was inserted into a Sfi1 enzyme site of the pcDNA3.1 vector.

TABLE 1

Primer sequence for preparing mesothelin scFv

| | Sequence |
|---|---|
| Mesothelin scFv Forward primer | 5'-GGCCCAGCCGGCCATGCAGGTACAACTGCA GCAG-3' (SEQ ID NO: 20) |
| Mesothelin scFv Reverse primer | 5'-GGCCCTTGGTGGAGGCACTCGAGACGGTGA CCAGGGTTC-3' (SEQ ID NO: 21) |

To prepare PD-L1 scFv, an amplification was performed through the PCR based on a primer sequence as shown in a following table 2 to obtain a PD-L1 scFv base sequence comprising a heavy chain of SEQ ID NO: 4 and a light chain of SEQ ID NO: 6, after which the ligation between the vector and the insertion was performed by means of the same method as the method for preparing the said vector, to which mesothelin scFv was bound, such that a resulting product was inserted into the Sfi1 enzyme site of the pcDNA3.1 vector.

TABLE 2

Primer sequence for preparing PD-L1 scFv

| | Sequence |
|---|---|
| PD-L1 scFv Forward primer | 5'-GGCCCAGCCGGCCATGCAGGTCCAACTTGTGCAGTC-3' (SEQ ID NO: 22) |
| PD-L1 scFv Reverse primer | 5'-GGCCCTTGGTGGACCAAGCTGGAGATCAAA-3' (SEQ ID NO: 23) |

To prepare Her2 scFv, the amplification was performed through the PCR based on a primer sequence as shown in a following table 3 to obtain a Her2 scFv base sequence comprising a heavy chain of SEQ ID NO: 9 and a light chain of SEQ ID NO: 11, after which the ligation between the vector and the insertion was performed by means of the same method as the method for preparing the said vector, to which mesothelin scFv was bound, such that a resulting product was inserted into the Sfi1 enzyme site of the pcDNA3.1 vector.

TABLE 3

Primer sequence for preparing Her2 scFv

| | Sequence |
|---|---|
| Her2 scFv Forward primer | 5'-GGCCCAGCCGGCCATGGAGGTTCAGCTGGTGGA-3' (SEQ ID NO: 24) |
| Her2 scFv Reverse primer | 5'-GGCCCTTGGTACCAAGGTGGAGATCAAA-3' (SEQ ID NO: 25) |

Also, to prepare CD19, MUC-1, EFGR and VEGFR scFv, a synthesis was performed on a base sequence for scFv (CD19 scFv comprising a heavy chain of SEQ ID NO: 29 and a light chain of SEQ ID NO: 31; MUC-1 scFv comprising a heavy chain of SEQ ID NO: 33 and a light chain of SEQ ID NO: 35; EGFR scFv comprising a heavy chain of SEQ ID NO: 37 and a light chain of SEQ ID NO: 39; and VEGFR scFv comprising a heavy chain of SEQ ID NO: 41 and a light chain of SEQ ID NO: 43) based on an amino acid sequence of each scFv, after which the ligation between the vector and the insertion was performed by means of the same method as the method for preparing the said vector, to which mesothelin scFv was bound, such that a resulting product was inserted into the Sfi1 enzyme site of the pcDNA3.1 vector.

CXCL16 and a furin cleavage site were amplified through the PCR based on a primer sequence as shown in a following table 4, and a Not1 enzyme site behind immunoglobulin present in the vector was used. The vector, into which scFv for recognizing a target antigen was inserted, was decomposed with a Not1 enzyme for two hours, and purified, after which the vector, the insertion, i.e. a CXCL16 sample, and a ligase enzyme were mixed together and cultured at 25° C. for two hours to perform the ligation between the vector and the insertion.

TABLE 4

Primer sequence for preparing CXCL16 and the furin cleavage site

| | Sequence |
|---|---|
| CXCL16, Furin cleavage site Forward primer | 5'-CACACTGGCGGCCGCACGGGTGAAGCGGAACGAGGGCAG-3' (SEQ ID NO: 26) |
| CXCL16, Furin cleavage site Reverse primer | 5'-AATCTCGAGCGGCCGCCTAAGGAAGTAAATGCTTCTGGTG-3' (SEQ ID NO: 27) |

Fusion polypeptide (NRP-body) was mass-produced by transfecting a CHO (Chinese hamster ovary) cell, from which furin was removed, with the prepared expression vector. The CHO cell transfected with the said expression vector was cultured in a 150 mm plate, then cultured in a roller bottle incubator for 72 hours, and then collected therefrom. A collected culture fluid was centrifuged, after which only supernatant thereof was purified by using a protein A-agarose column of an AKTA protein purification system (GE Healthcare Life Sciences), such that the fusion polypeptide was produced.

<Example 3> Identification of Binding of the Fusion Polypeptide to an Antigen

Mesothelin-recognizing fusion polypeptide (mesothelin scFv NRP-body) (0.1-2 μg/ml) prepared in Example 2 above was divided into $2 \times 10^5$ Panc-1 cells, which are pancreatic cancer cell lines, and cultured at 4° C. for 20 minutes. After that, the cells were collected therefrom and washed with PBS, after which FC antibodies (1 μg/ml), to which FITC was bound, were divided thereto and cultured at 4° C. for 20 minutes. After that, the cells were collected therefrom again, then washed with PBS, and then analyzed by means of an FACS.

Figure 3:
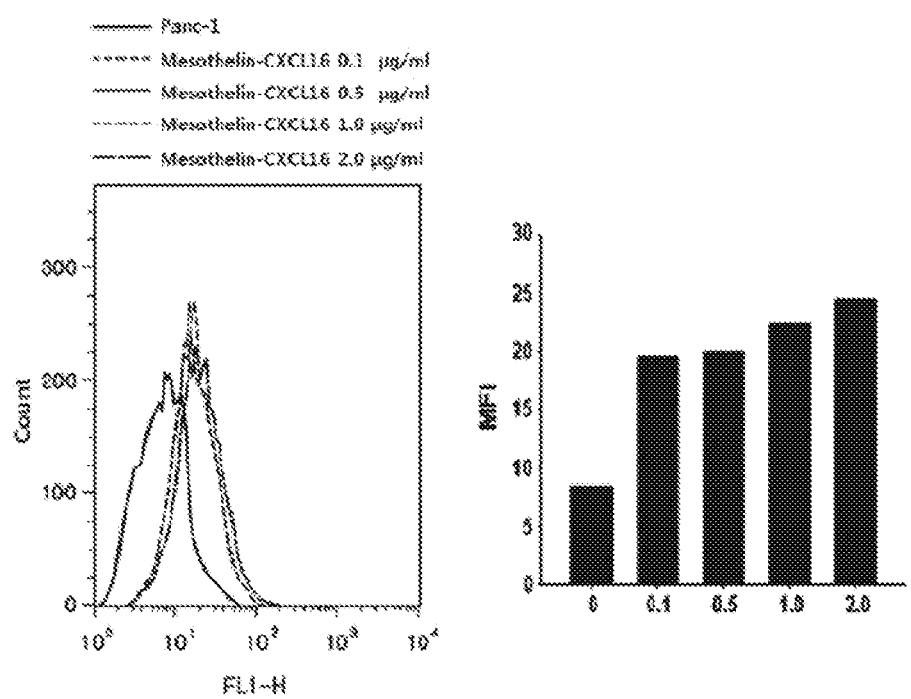
FIG. 3 is a graph of showing results of identifying that the fusion polypeptide prepared according to the present invention recognizes and binds to mesothelin present on a surface of a pancreatic cancer cell line by means of a mesothelin-recognizing site.

The results thereof were shown in FIG. 3.

As identified in FIG. 3, it was identified that mesothelin present on a surface of the pancreatic cancer cell line is recognized through a mesothelin-recognizing site of the fusion polypeptide prepared in Example 2 above, such that the fusion polypeptide is bound to the cell surface.

Figure 4:
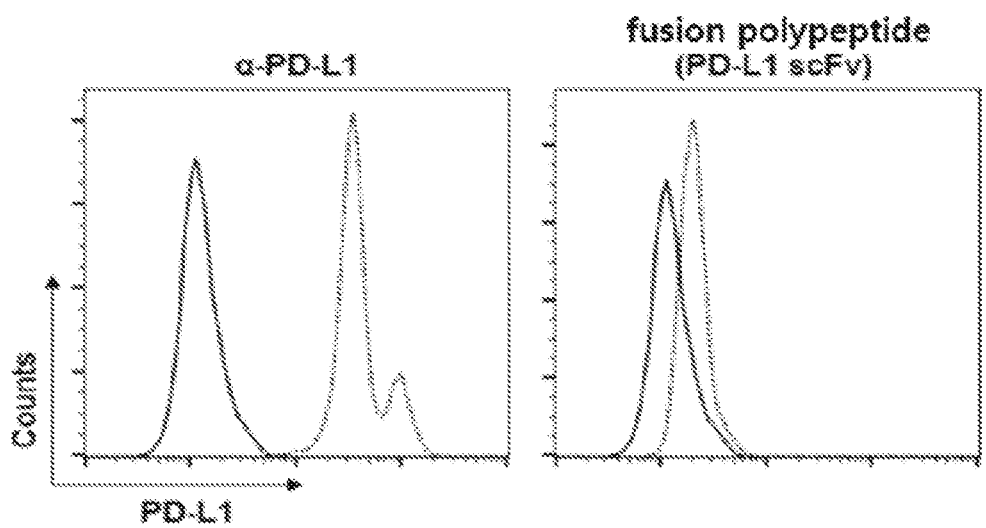
FIG. 4 is a graph of showing results of identifying that the fusion polypeptide prepared according to the present invention recognizes and binds to PD-L1 present on a surface of a pancreatic cancer cell line by means of a PD-L1-recognizing site.
Figure 5:
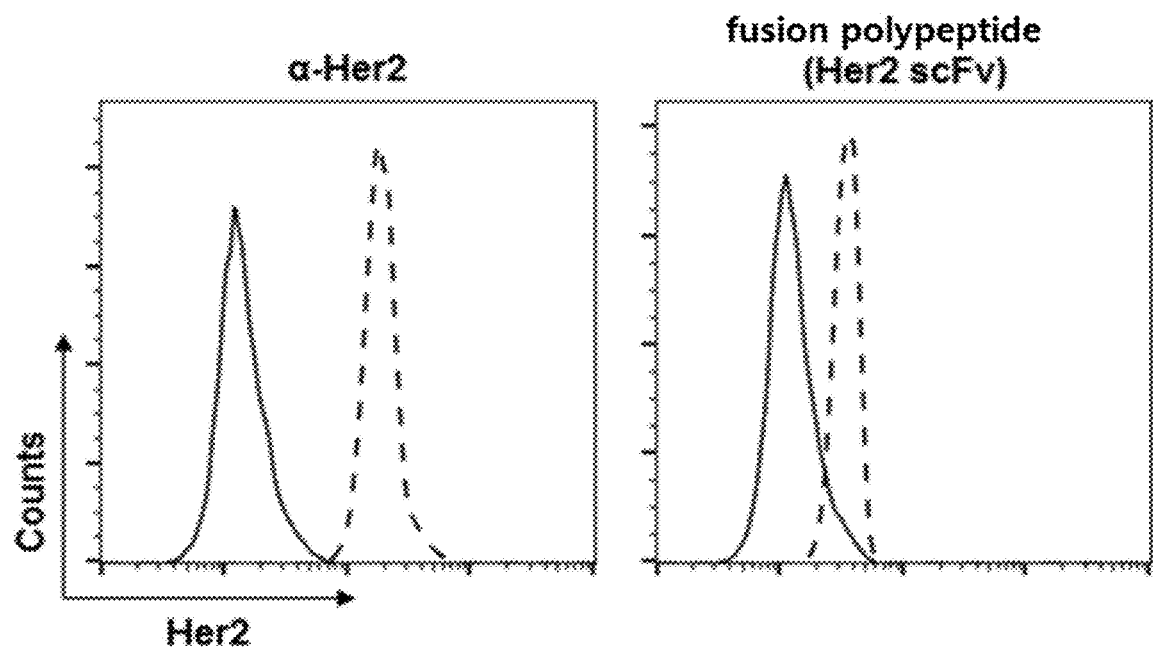
FIG. 5 is a graph of showing results of identifying that the fusion polypeptide prepared according to the present invention recognizes and binds to Her2 present on a surface of a pancreatic cancer cell line by means of a Her2-recognizing site.

Also, in order to identify that the fusion polypeptide of the present invention is bound to a surface of a target cell line, even if antigen-recognizing sites are different, the FACS analysis was performed even on the PD-L1 scFv fusion polypeptide and Here scFv fusion polypeptide, which were prepared in Example 2 above, under the same condition as the experiment on antigen-binding of the said mesothelin scFv fusion polypeptide, wherein the results thereof were shown in FIG. 4 (PD-L1 scFv NRP-body) and FIG. 5 (Her2 scFv NRP-body).

As identified in FIGS. 4 and 5, it was identified that the PD-L1 scFv NRP-body and the Her2 scFv NRP-body recognize PD-L1 or Her2 present on a surface of a pancreatic cancer cell line respectively through an antigen-recognizing site, and the fusion polypeptide is specifically bound to the cell surface, and thus identified for the fusion polypeptide of the present invention that the antibody specifically binding to a target antigen may be differently applied depending on a target tumor-associated antigen.

<Example 4> Identification of Characteristics of CXCL16 Release

Through a human CXCL16 ELISA, it was identified if a furin cleavage site of the fusion polypeptide (NRP-body)

prepared in Example 2 above is cleaved by means of the furin of a cancer cell line and CXCL16 is released.

The CXCL16 ELISA was performed according to a method of Human CXCL16 ELISA kit (# DCX160) of an R&D system. For an ELISA analysis, the mesothelin scFv fusion polypeptide (mesothelin scFv NRP-body) was divided in an amount of 0.5 µg/mL and 50 µl/well into a 96-well plate for ELISA (R&D) and left alone at room temperature for two hours, such that a resulting absorbed one was used for that analysis. The said plate was washed, after which a peroxidase label was added thereto in an amount of 200 µl/well as a secondary antibody, and left alone at room temperature for two hours. The said plate was washed with Tween-PBS, after which an ABTS substrate solution was added thereto to carry out color development, such that an absorbance was measured at OD 415 nm by using a plate reader.

Figure 6:
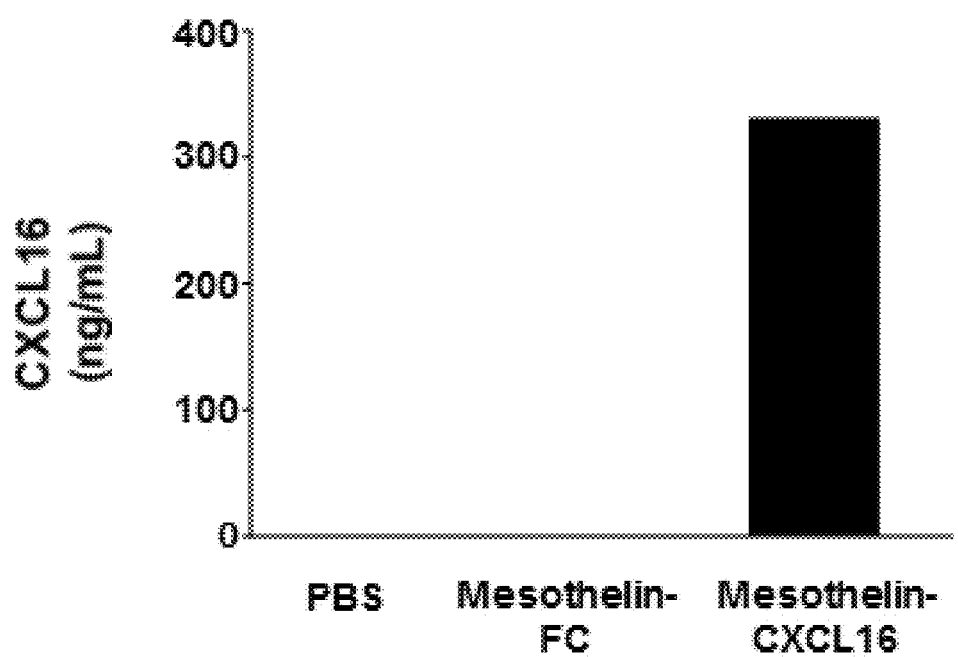
FIG. 6 is a graph of showing results of identifying that the fusion polypeptide prepared according to the present invention binds to a pancreatic cancer cell line to release CXCL16.

The results thereof were shown in FIG. 6.

As identified in FIG. 6, it was identified that the fusion polypeptide (NRP-body) is bound to mesothelin of a pancreatic cancer cell line, i.e. Panc-1, after which a furin cleavage site of the fusion polypeptide is cleaved by means of furin of the cancer cell, such that CXCL16 is released.

<Example 5> Identification of an Increase in Migration Ability (Influx) of NK Cells by Means of CXCL16 Released from the Fusion Polypeptide A Boyden chamber system was used to identify if the fusion polypeptide prepared in Example 2 above recognizes and binds to cancer expressing a target antigen, after which CXCL16, a protein for inducing an influx of NK cells, is released to increase an influx of the NK cells.

HPDE, Panc-1 (ATCC, Cat.CRL-1469), HCT116 (ATCC, Cat.CCL-247), MCF7 (ATCC, Cat.HTB-22) and HT-29 (ATCC, Cat.HTB-38) cell lines were divided by 2×10$^5$ onto a bottom layer of a Boyden Chamber assay plate (Fisher Scientific, #07-200-155), and cultured in a $CO_2$ incubator at 37° C. for two hours. The mesothelin scFv-fusion polypeptide was divided in an amount of 1 µg/ml into each cell line above, and cultured in the $CO_2$ incubator at 37° C. for four hours. The NK cells were labeled with CFSE (BioLegend, # RUO 423801), then divided by 2×10$^5$ onto an upper layer, and then cultured in the $CO_2$ incubator at 37° C. for four hours. After that, the cells were collected from the bottom layer, and a distribution of CFSE-labeled NK cells was identified through the FACS.

Figure 7:
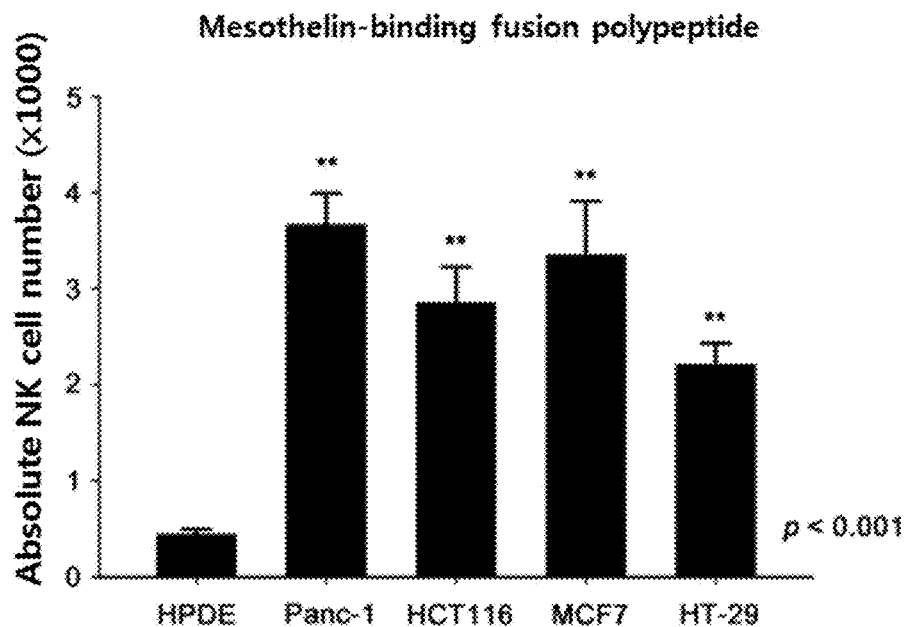
FIG. 7 is a graph of showing results of identifying that a migration ability of NK cells is increased according to treatment of various cancer cell lines with the fusion polypeptide of the present invention, comprising an antibody binding to mesothelin.

The results thereof were shown in FIG. 7.

As identified in FIG. 7, it was identified that a migration ability of human expanded NK cells is increased by means of CXCL16 released from the mesothelin scFv fusion polypeptide, and further identified that a degree of increased influx of the NK cells varies depending on a type of cancer cell line.

Figure 8:
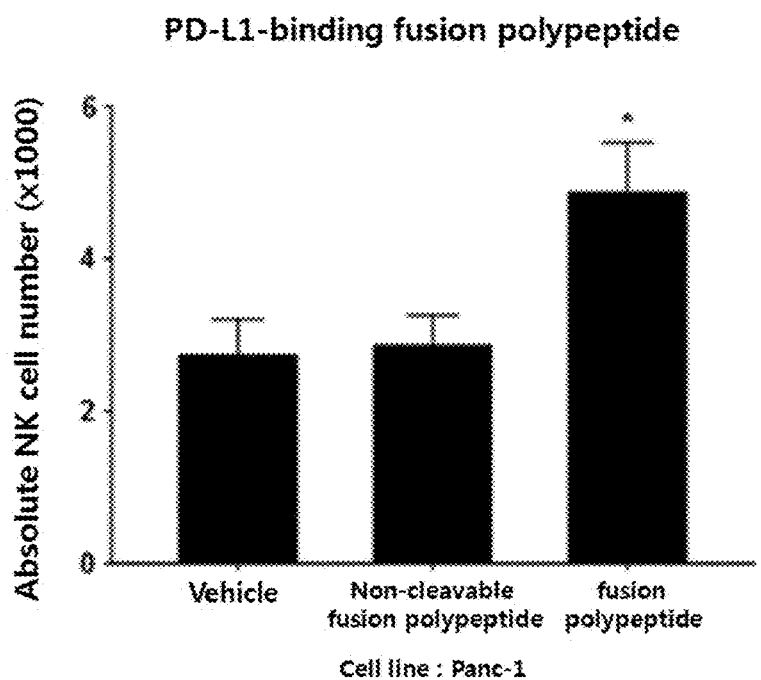
FIG. 8 is a graph of showing results of identifying that an influx of NK cells is increased according to treatment of a Panc-1 cell line with the fusion polypeptide of the present invention, comprising an antibody binding to PD-L1.
Figure 9:
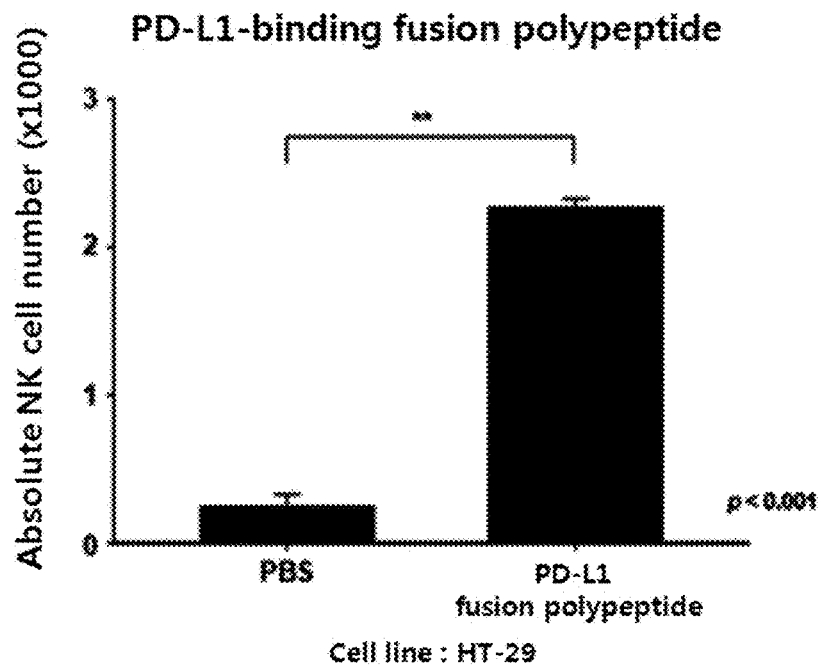
FIG. 9 is a graph of showing results of identifying that the influx of NK cells is increased according to treatment of an HT-29 cell line with the fusion polypeptide of the present invention, comprising an antibody binding to PD-L1.
Figure 10:
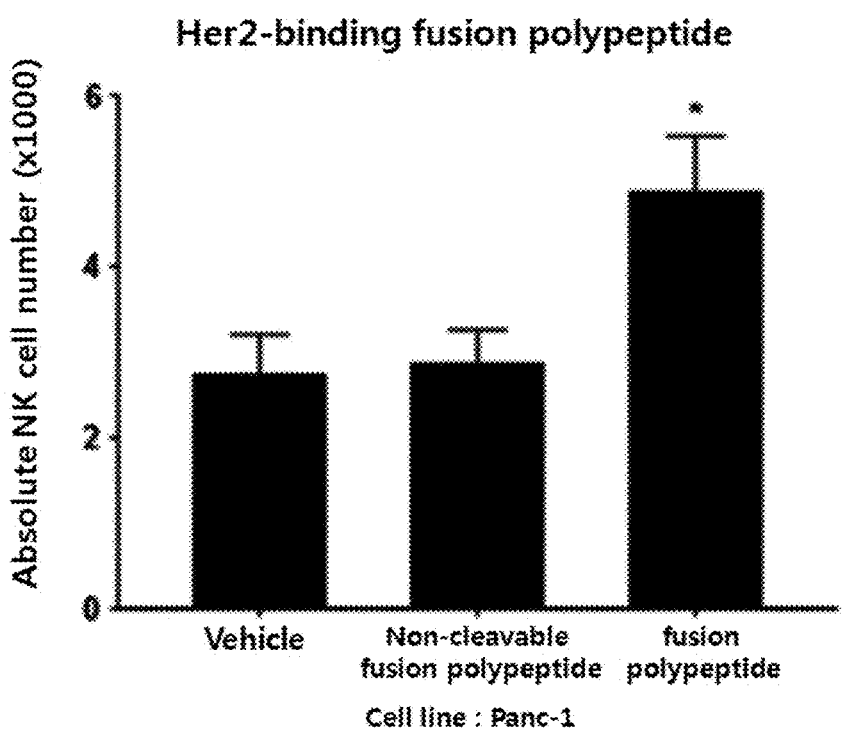
FIG. 10 is a graph of showing results of identifying that the influx of NK cells is increased according to treatment of a Panc-1 cell line with the fusion polypeptide of the present invention, comprising an antibody binding to Her2.
Figure 11:
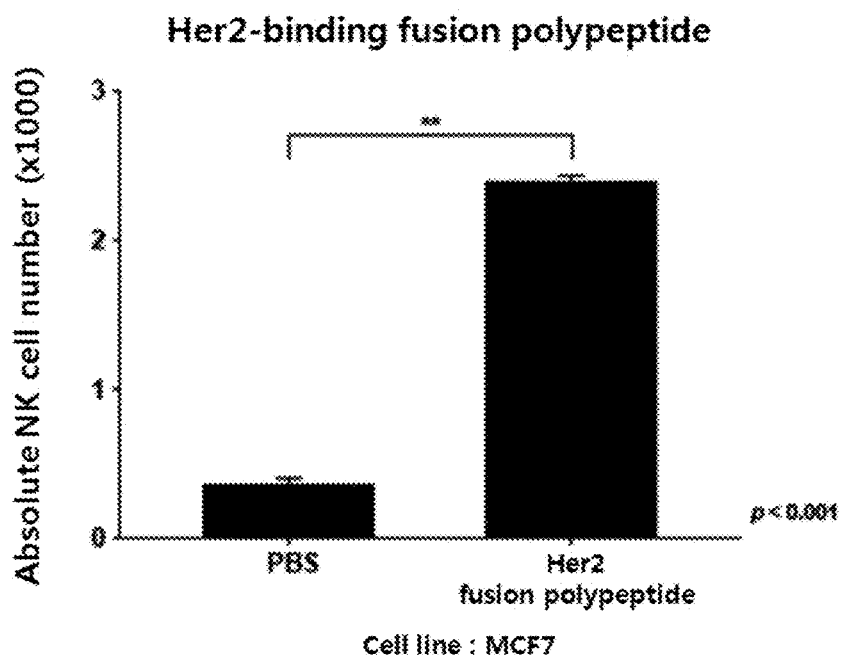
FIG. 11 is a graph of showing results of identifying that the influx of NK cells is increased according to treatment of an MCF7 cell line with the fusion polypeptide of the present invention, comprising an antibody binding to Her2.

Also, the PD-L1 scFv-fusion polypeptide and the Her2 scFv-fusion polypeptide prepared in Example 2 above were divided into Panc-1, HT-29 or MCF7 cell lines, and thus identified that an influx of the NK cells is increased through the Boyden chamber system under the same condition as in the experiment on the said mesothelin scFv-fusion polypeptide, wherein the results thereof were shown in FIG. 8 (PD-L1 scFv NRP-body for Panc-1), FIG. 9 (PD-L1 NRP-body for HT-29), FIG. 10 (Her2 NRP-body for Panc-1) and FIG. 11 (Her2 scFv NRP-body for MCF7).

As identified in FIGS. 8 to 11, it was identified that the migration ability of the human expanded NK cells is increased by means of CXCL16 released from each fusion polypeptide just like the mesothelin scFv-fusion polypeptide.

Figure 12:
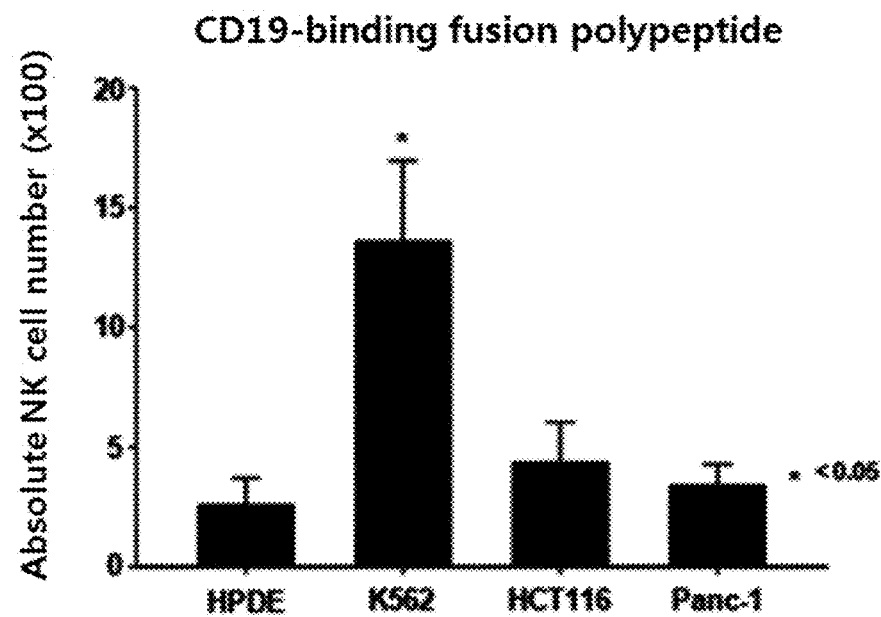
FIG. 12 is a graph of showing results of identifying that a migration ability of NK cells is increased according to treatment of various cancer cell lines with the fusion polypeptide of the present invention, comprising an antibody binding to CD19.
Figure 13:
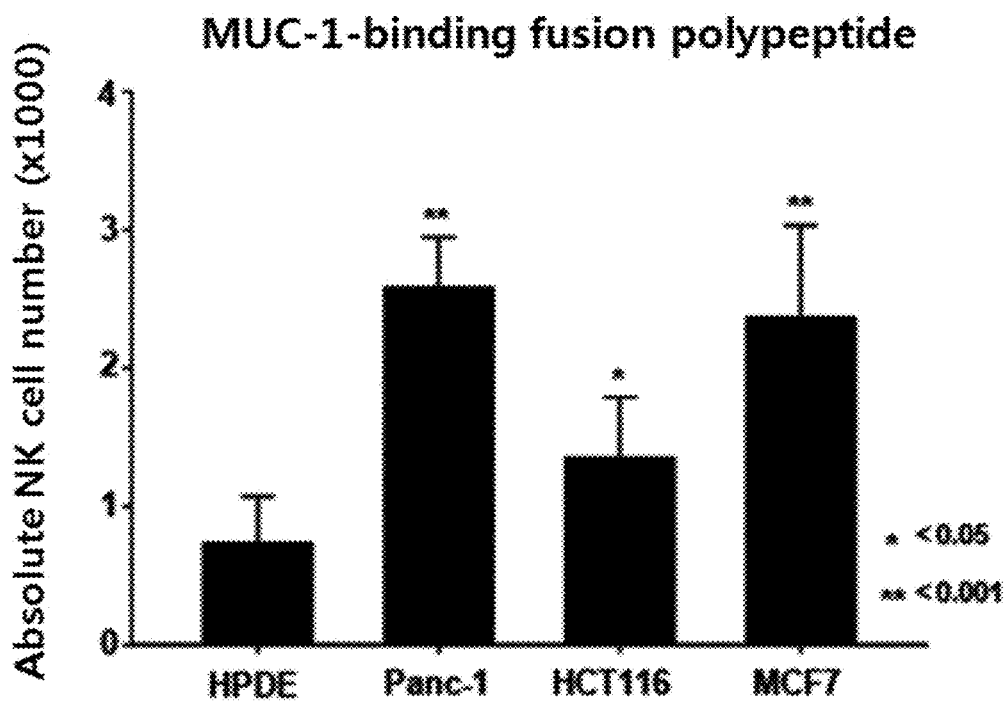
FIG. 13 is a graph of showing results of identifying that the migration ability of NK cells is increased according to treatment of various cancer cell lines with the fusion polypeptide of the present invention, comprising an antibody binding to MUC-1.
Figure 14:
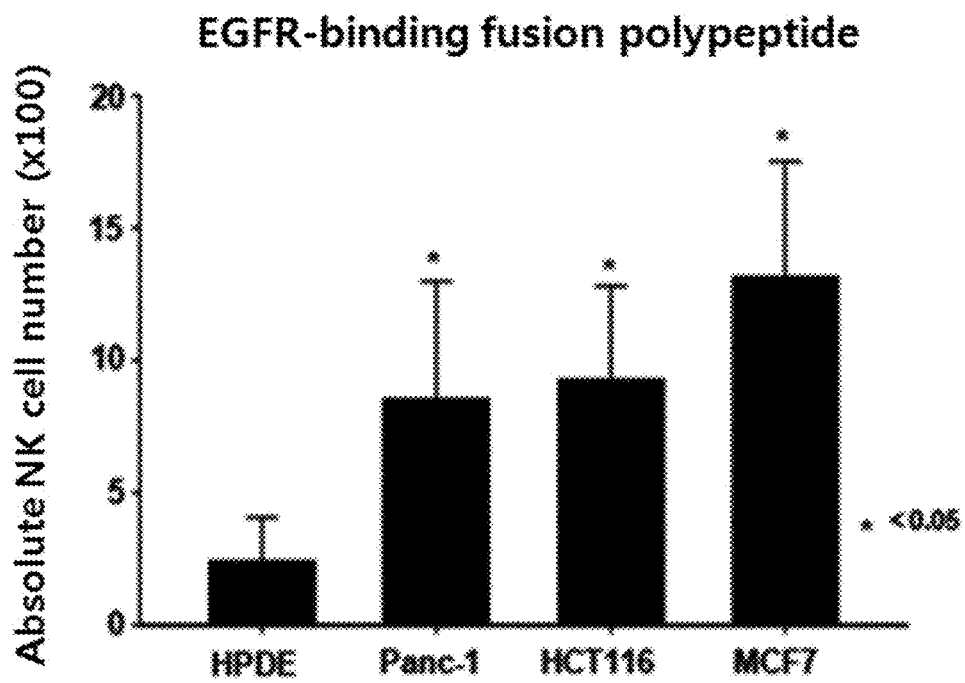
FIG. 14 is a graph of showing results of identifying that the migration ability of NK cells is increased according to treatment of various cancer cell lines with the fusion polypeptide of the present invention, comprising an antibody binding to EGFR.
Figure 15:
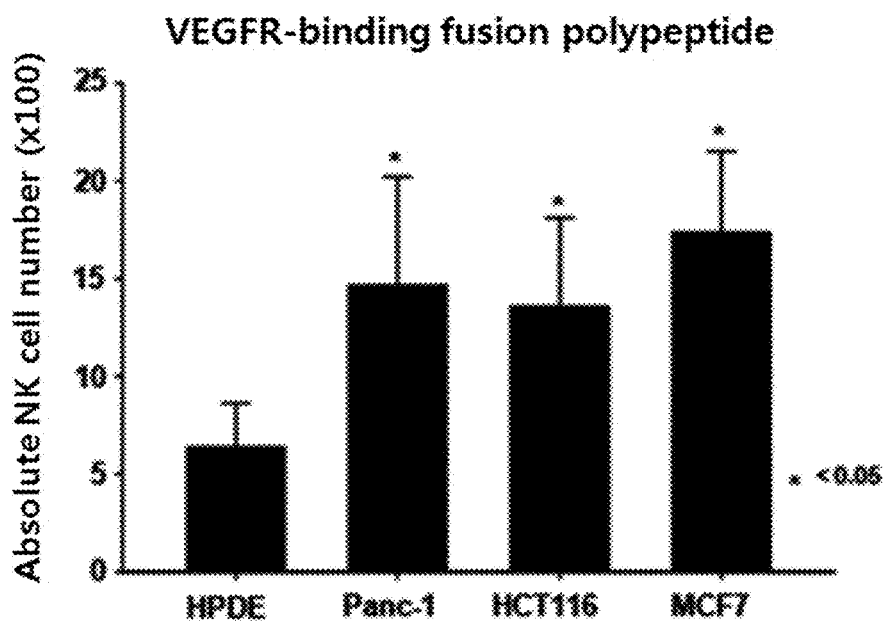
FIG. 15 is a graph of showing results of identifying that the migration ability of NK cells is increased according to treatment of various cancer cell lines with the fusion polypeptide of the present invention, comprising an antibody binding to VEGFR.
Figure 16:
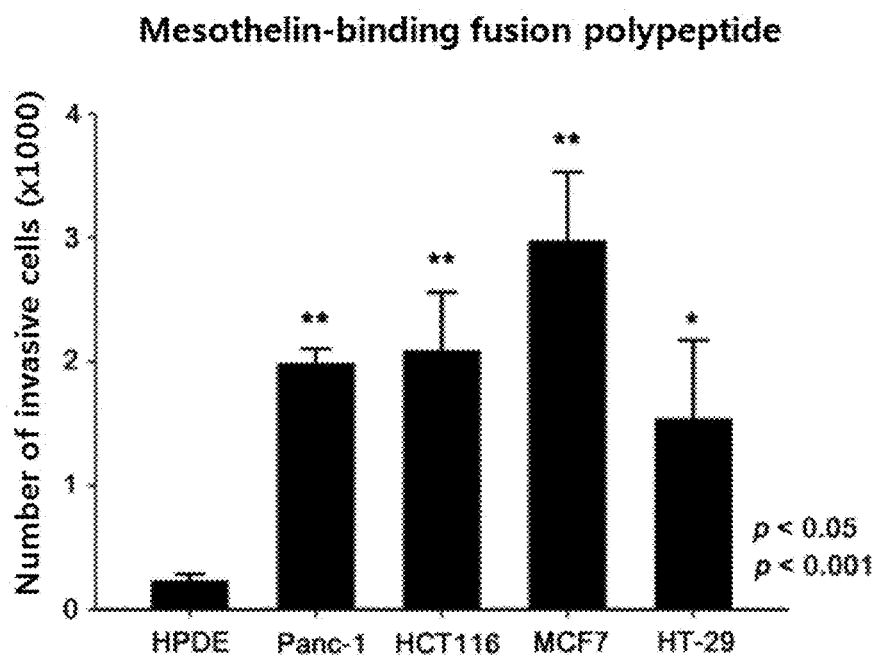
FIG. 16 is a graph of showing results of identifying that an invasion ability of NK cells is increased according to treatment of various cancer cell lines with the fusion polypeptide of the present invention, comprising an antibody binding to mesothelin.
Figure 17:
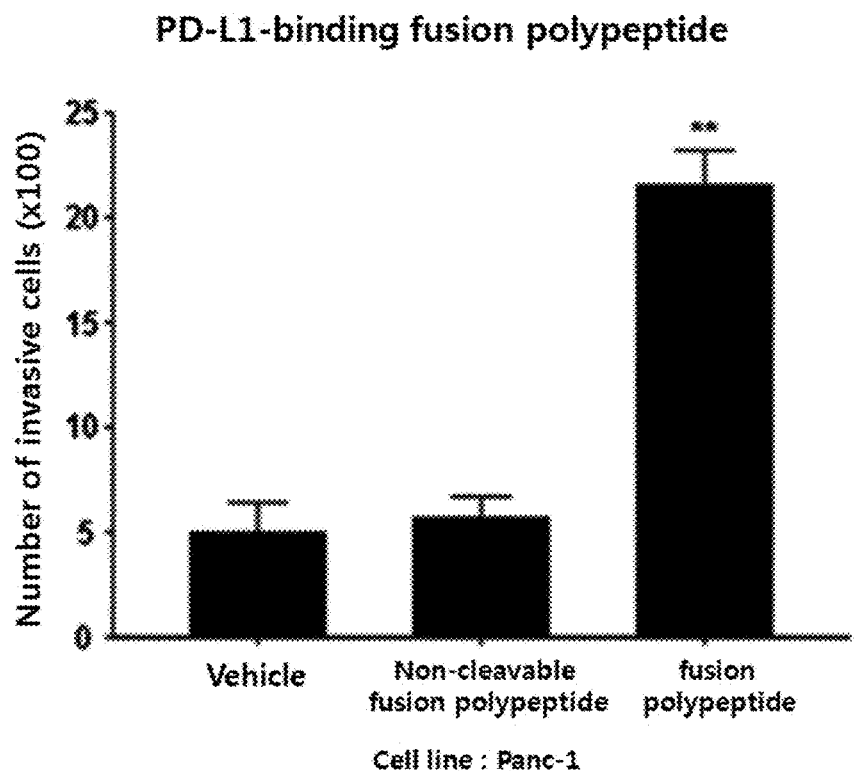
FIG. 17 is a graph of showing results of identifying that the invasion ability of NK cells is increased according to treatment of a Panc-1 cell line with the fusion polypeptide of the present invention, comprising an antibody binding to PD-L1.
Figure 18:
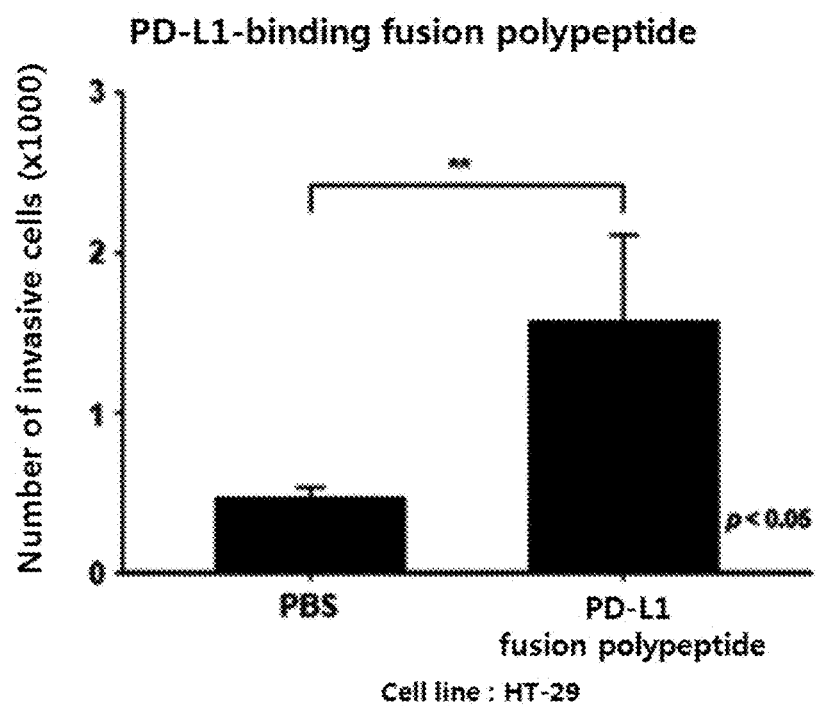
FIG. 18 is a graph of showing results of identifying that the invasion ability of NK cells is increased according to treatment of an HT-29 cell line with the fusion polypeptide of the present invention, comprising an antibody binding to PD-L1.
Figure 19:
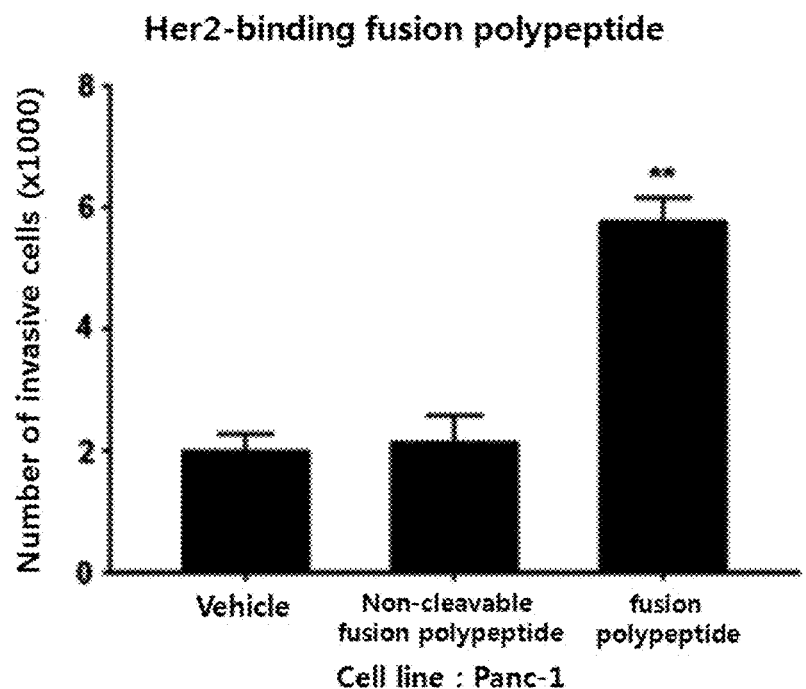
FIG. 19 is a graph of showing results of identifying that the invasion ability of NK cells is increased according to treatment of a Panc-1 cell line with the fusion polypeptide of the present invention, comprising an antibody binding to Her2.
Figure 20:
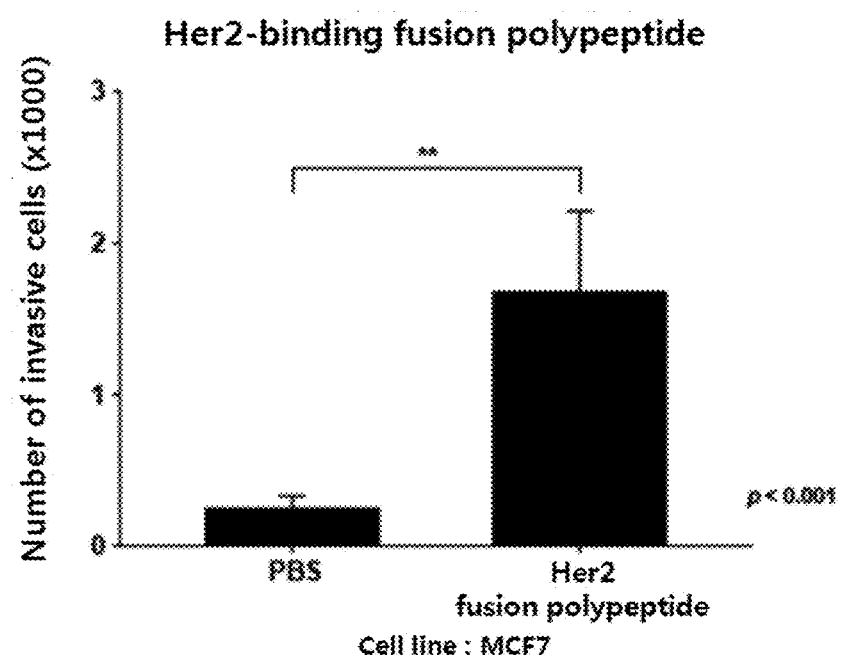
FIG. 20 is a graph of showing results of identifying that the invasion ability of NK cells is increased according to treatment of an MCF7 cell line with the fusion polypeptide of the present invention, comprising an antibody binding to Her2.
Figure 21:
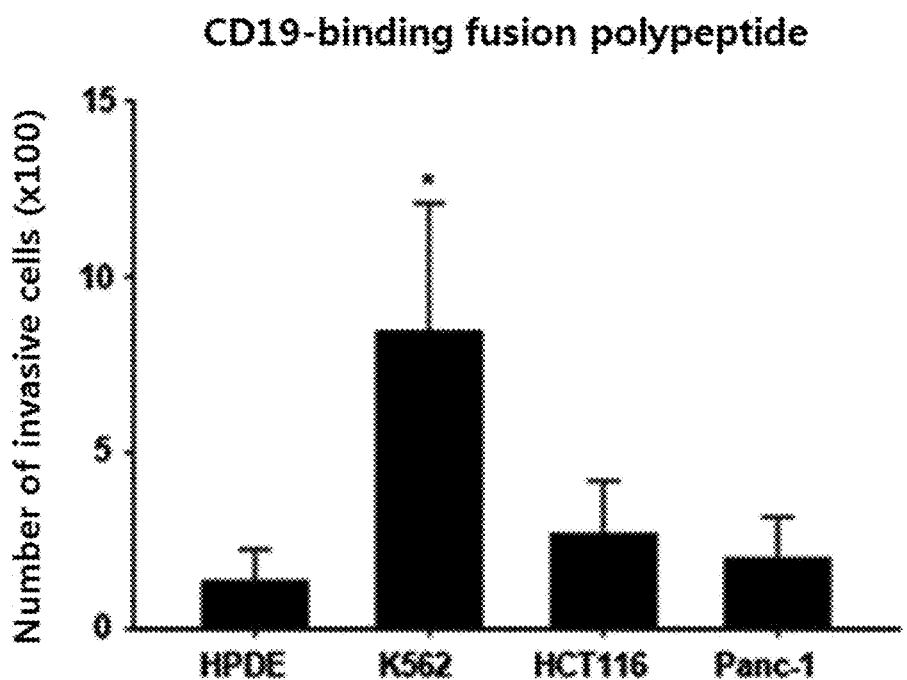
FIG. 21 is a graph of showing results of identifying that the invasion ability of NK cells is increased according to treatment of various cancer cell lines with the fusion polypeptide of the present invention, comprising an antibody binding to CD19.
Figure 22:
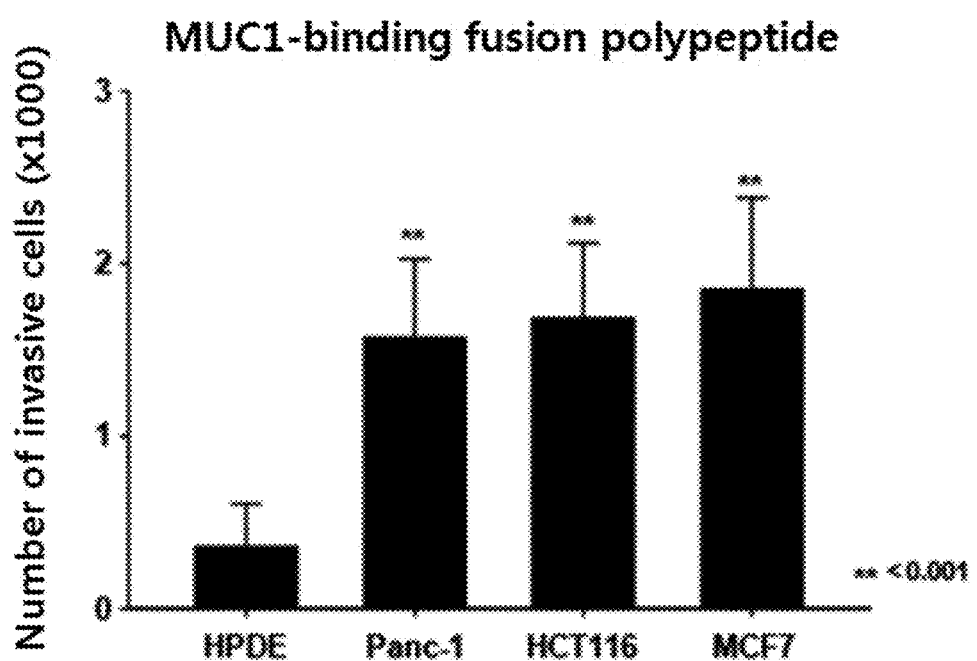
FIG. 22 is a graph of showing results of identifying that the invasion ability of NK cells is increased according to treatment of various cancer cell lines with the fusion polypeptide of the present invention, comprising an antibody binding to MUC-1.
Figure 23:
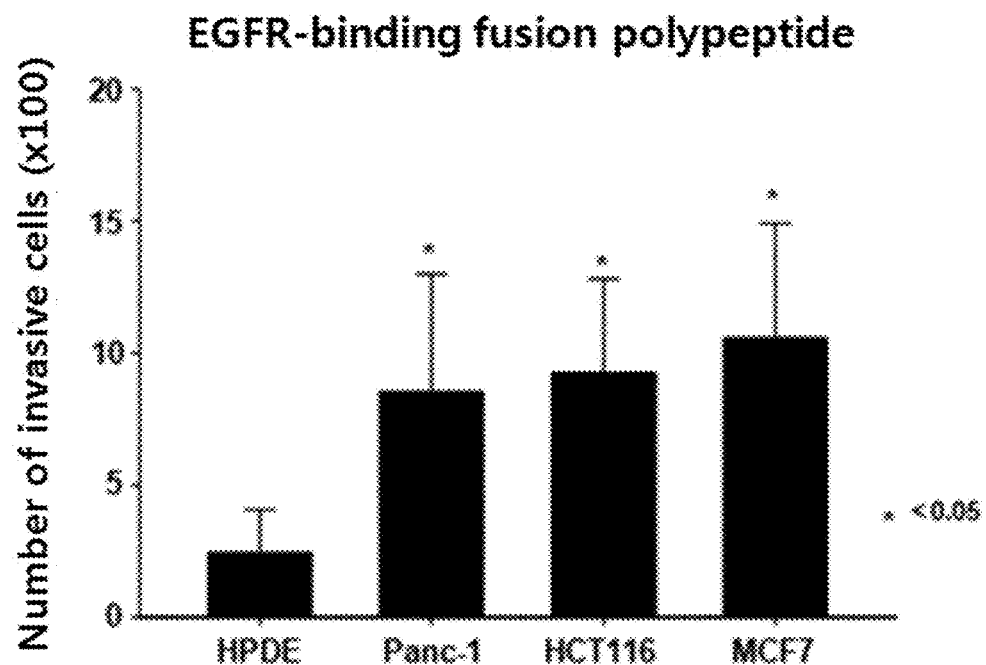
FIG. 23 is a graph of showing results of identifying that the invasion ability of NK cells is increased according to treatment of various cancer cell lines with the fusion polypeptide of the present invention, comprising an antibody binding to EGFR.
Figure 24:
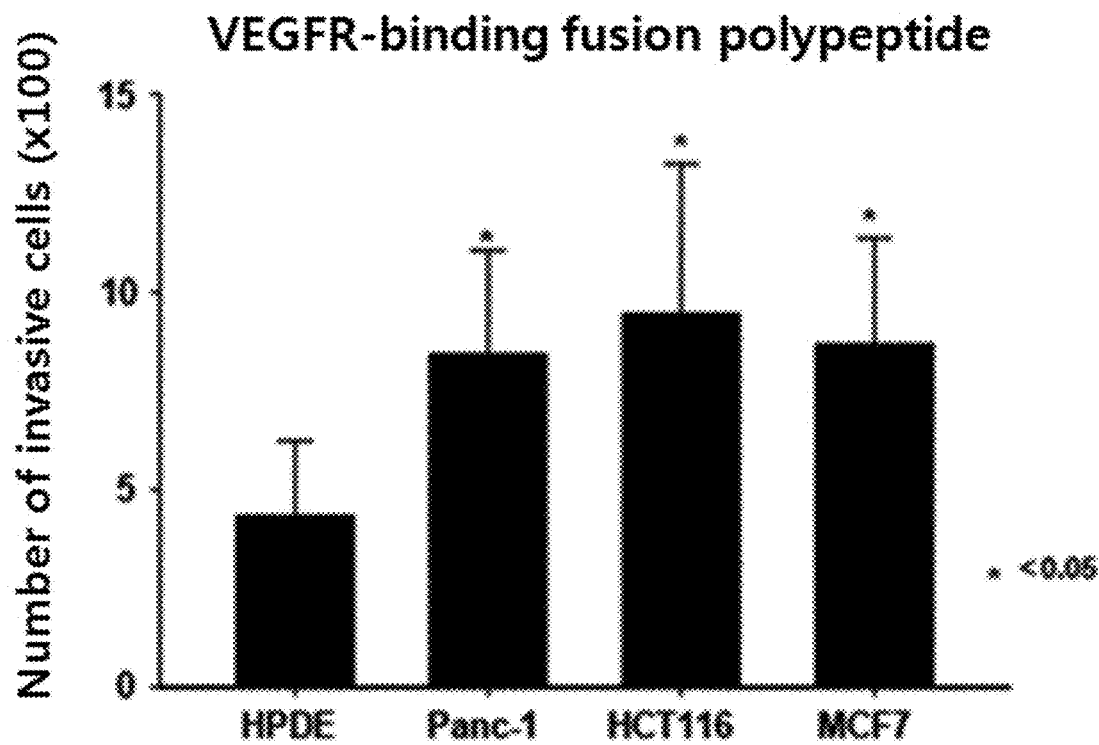
FIG. 24 is a graph of showing results of identifying that the invasion ability of NK cells is increased according to treatment of various cancer cell lines with the fusion polypeptide of the present invention, comprising an antibody binding to VEGFR.

Also, the CD-19, MUC-1, EGFR and VEGFR scFv-fusion polypeptides prepared in Example 2 above were divided into HPDE, K562 (ATCC, Cat.CCL-243), HCT116 (ATCC, Cat.CCL-247), Panc-1 (ATCC, Cat.CRL-1469) or MCF7 (ATCC, Cat.HTB-22) cell lines, and thus identified whether an influx of the NK cells is increased or not under the same condition as in the experiment on the said mesothelin scFv-fusion polypeptide through the Boyden chamber system, wherein the results thereof were shown in FIG. 12 (CD19 scFv NRP-body), FIG. 13 (MUC-1 scFv NRP-body), FIG. 14 (EGFR scFv NRP-body) and FIG. 15 (VEGFR scFv NRP-body), respectively.

As identified in FIGS. 12 to 15, it was identified that the migration ability of the human expanded NK cells is increased by means of CXCL16 released from the fusion polypeptide, and further identified that a degree of increased influx of the NK cells varies depending on a type of cancer cell line.

<Example 6> Identification of an Invasion Ability of NK Cells by CXCL1.6 Released from the Fusion Polypeptide An invasion assay was used to identify if each fusion polypeptide prepared in Example 2 above recognizes and binds to a target antigen expressed on a cancer cell, after which CXCL16, a protein for inducing an influx of NK cells, is released to increase an invasion ability of the NK cells into cancer cells.

Particularly, HPDE, Panc-1, HCT116, MCF7, HT-29 and K562 cell lines were divided by 2×10$^5$ onto a bottom layer of the Boyden Chamber assay plate (Fisher Scientific, #07-200-155), and cultured in a $CO_2$ incubator at 37° C. for two hours, after which the fusion polypeptide prepared in Example 2 was divided in an amount of 1 µg/ml into each cell line above. The upper layer was treated with matrigel (BD, #354234), after which the NK cells were divided by 2×10$^5$ thereto, and cultured in the $CO_2$ incubator at 37° C. for 48 hours. After that, the upper layer was collected therefrom and stained with crystal violet for one hour, after which a picture was randomly taken from three portions of the upper layer, such that the invasion ability of the NK cells was measured by means of an image J program.

The results of each fusion polypeptide were shown in FIGS. 16 to 24, respectively.

As identified in FIGS. 16 to 24, it was identified that the invasiveness of human expanded NK cells is increased by means of CXCL16 released from the fusion polypeptide, and further identified that a degree of increased invasion ability of the NK cells varies depending on a type of cancer cell line.

<Example 7> Identification of an Induced Death of Cancer Cell Lines by Increasingly Introduced NK Cells It was identified about an efficacy of antibody-dependent cellular cytotoxicity (ADCC) on inducing a death of cancer cell lines by means of NK cells, which are increasingly introduced after a release of CXCL16 from the fusion polypeptide prepared in Example 2 above.

Panc-1 cell lines were divided by 2×10$^5$ into a 96-well plate, and cultured in a $CO_2$ incubator at 37° C. for two hours. The target cells were treated with the mesothelin scFv-fusion polypeptide in an amount of 1 µg/ml, and cultured in the $CO_2$ incubator at 37° C. for two hours. The NK cells were added thereto by $2\times10^5$ to set a ratio of target cell and effector cell at 1:1, and cultured in the $CO_2$ incubator at 37° C. for four hours. The cells were collected therefrom, then washed with PBS, then stained with Annexin V (1 µg/ml) and PI (1 µg/ml) for 30 minutes, and then analyzed with the FACS.

Figure 25:
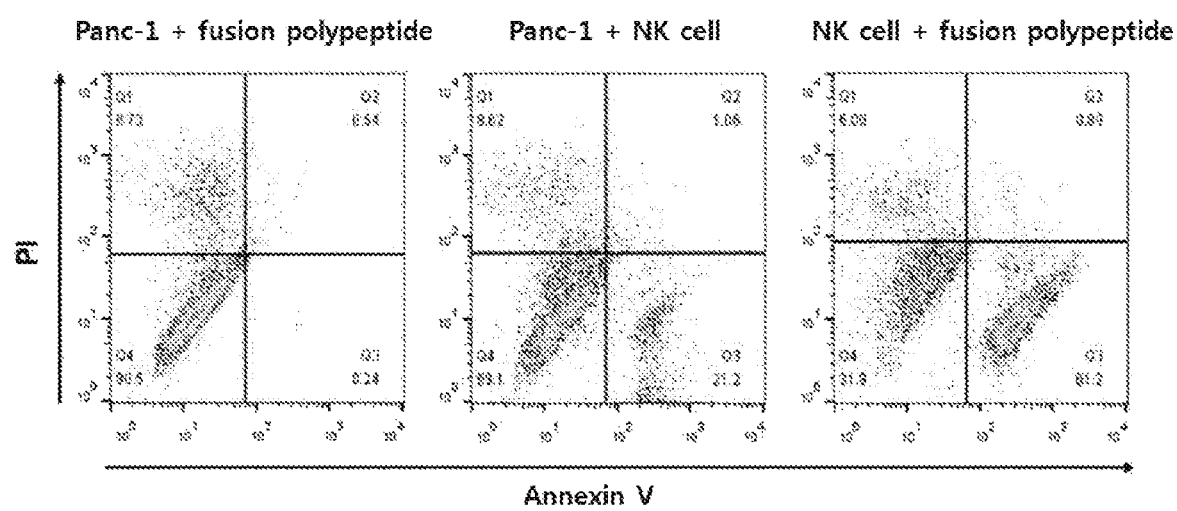
FIG. 25 is a graph of showing results of identifying that the invasion ability of NK cells is increased by means of a fusion polypeptide (Her2 scFv NRP-body) prepared to recognize Her2 according to the present invention.

The results thereof were shown in FIG. 25.

As identified in FIG. 25, it was identified that the death of cancer cells is remarkably increased by means of the NK cells, which are increasingly introduced after a release of CXCL16.

<Example 8> Identification of a Therapeutic Efficacy of the Fusion Polypeptide in an Animal Model with Transplanted Cancer The fusion polypeptide prepared in Example 2 was injected into an animal model with transplanted cancer to identify an effect thereof in vivo.

For an in vivo experiment, a six-week female NSG (NOD.Cg-PrkdcscidIl2rgtm1wjl/SzJ) mouse was used. The management of mice was performed under the authority of the Animal Care Committee of the Laboratory Animal Resource Center in the Korea Research Institute of Bioscience and Biotechnology. Panc-1 was injected into a mouse pancreas, after which a tumor was formed for two weeks, and mesothelin, PD-L1 or Her2 scFv fusion polypeptide (5 mg/kg) was intraperitoneally injected at an interval of five days.

For an experiment on tumor growth, the NK cells were I.V. injected in an amount of $1\times10^7$/mouse. For a tumor growth observation, a growth of Panc-1, which expresses luciferase, was observed by using an IVIS Living Image 3.0 program. For an experiment on the migration ability of the NK cells, the NK cells stained with DiR were intravenously injected in an amount of $1\times10^7$/mouse and observed with the IVIS fluorescence Image program and FACS.

Figure 26A:
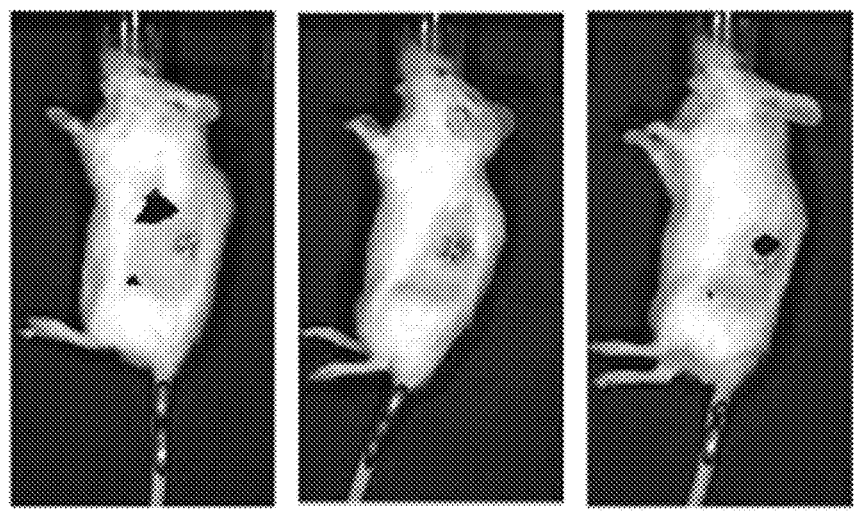
FIG. 26A is a diagram showing that an influx of natural killer cells into cancer tissues is greatly increased by NRP-body.
Figure 26B:
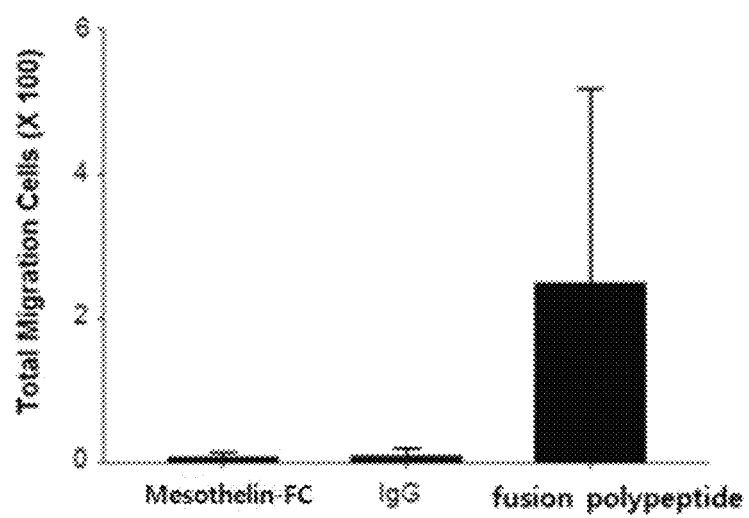
FIG. 26B is a diagram showing a total number of influx cells by the addition of NRP-body.
Figure 27A:
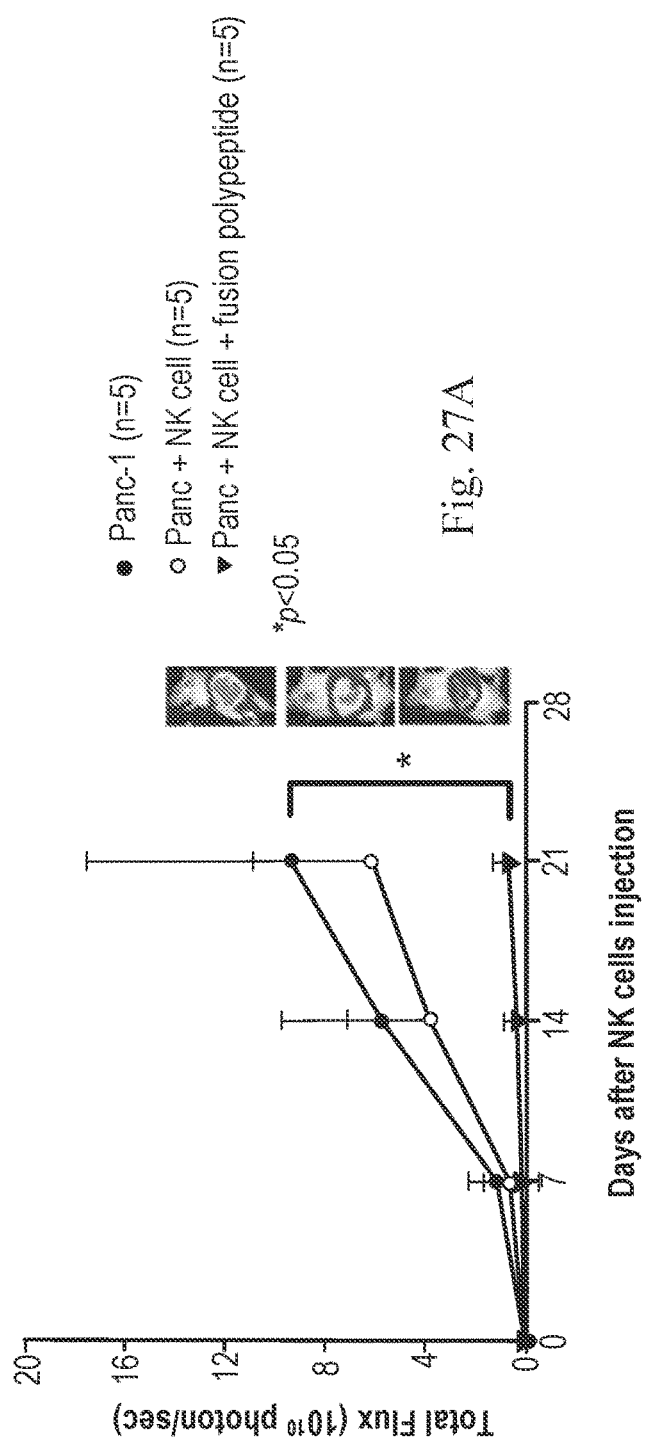
FIG. 27A is a diagram showing results of identifying the tumor growth inhibitory effect after administering a fusion polypeptide prepared in Example 2 together with natural killer cells.
Figure 27B:
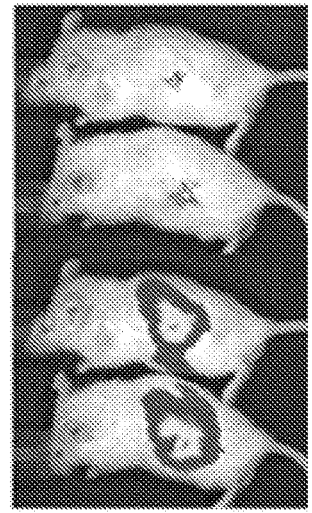
FIG. 27B is a diagram showing results of identifying an increase in migration of NK cells in tumor tissues with a fluorescence Image program.
Figure 27B:
Figure 27B:
Figure 28A:
FIG. 28A is a diagram showing results of identifying an increase in migration of NK cells in tumor tissues with a fluorescence Image program after administering a fusion polypeptide prepared in Example 2 together with natural killer cells.
Figure 28B:
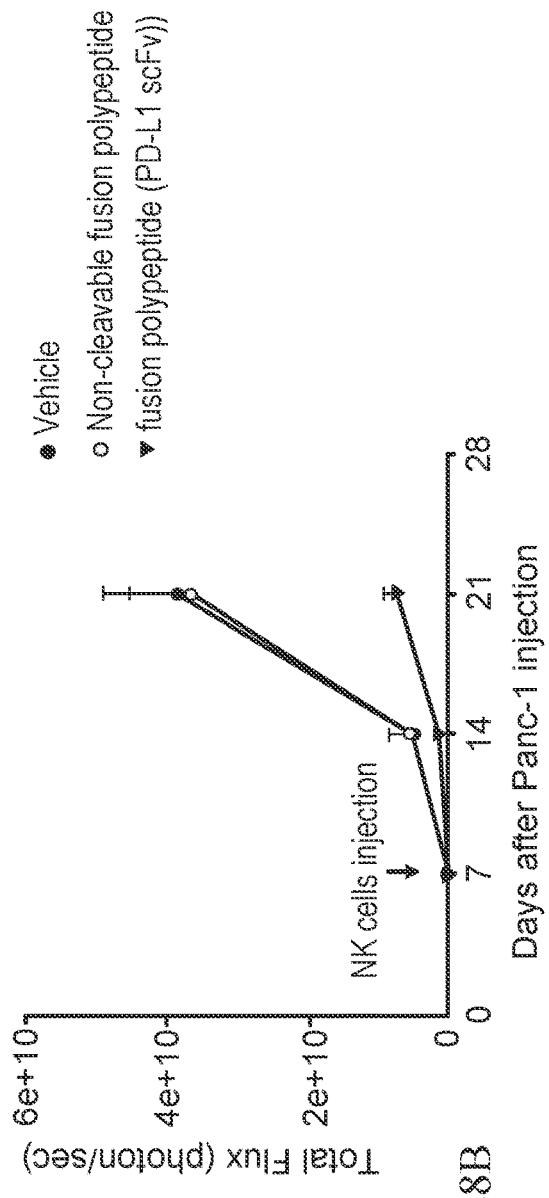
FIG. 28B is a diagram showing results of identifying the tumor growth inhibitory effect.
Figure 29A:
FIG. 29A is a diagram showing results of identifying an increase in migration of NK cells in tumor tissues with a fluorescence Image program after administering a fusion polypeptide prepared in Example 2 together with natural killer cells.
Figure 29B:
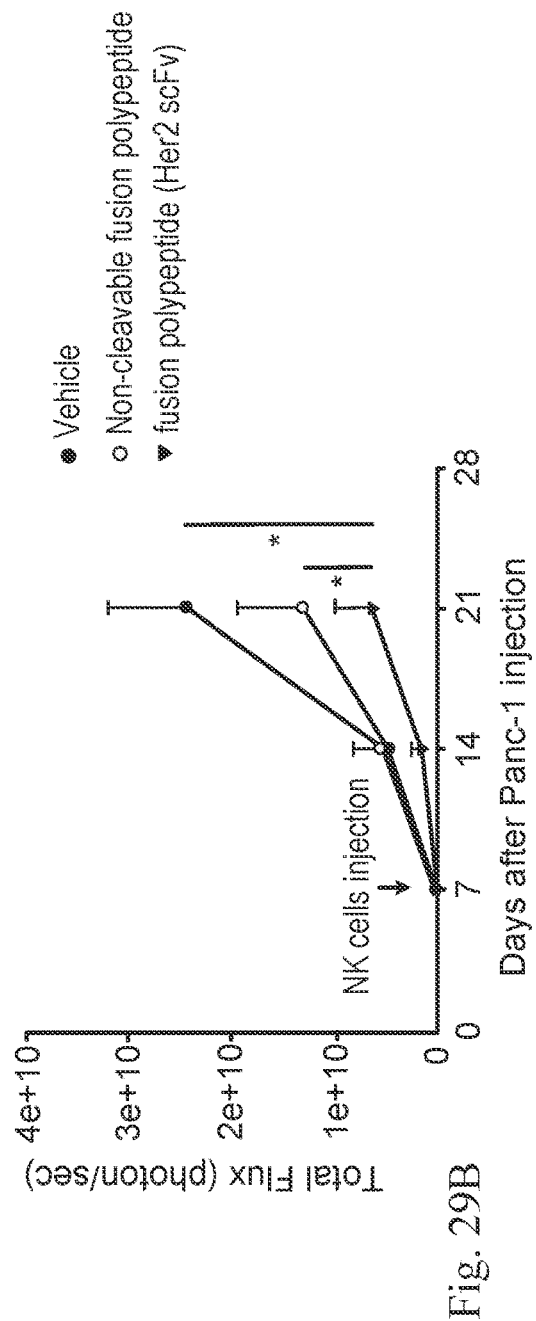
FIG. 29B is a diagram showing results of identifying the tumor growth inhibitory effect.

The results thereof were shown in FIGS. 26 to 29. FIG. 26 shows an induction of the NK cells into a cancer tissue according to an administration of the fusion polypeptide prepared in Example 2 above as well as the NK cells, and FIGS. 27, 28 and 29 show results of identifying a therapeutic effect by administering mesothelin scFv NRP-body, PD-L1 scFv NRP-body and Her2 scFv NRP-body respectively along with the NK cells.

As identified in A of FIG. 26, the influx of the NK cells into the cancer tissue was greatly increased by means of the NRP-body. As shown in B of FIG. 26, such agonistic effect occurred only with an addition of the NRP-body.

Also, as identified in FIGS. 27 to 29, in case of administering the fusion polypeptide prepared in Example 2 along with the NK cells, the tumor growth was remarkably inhibited, and the migration of the NK cells into the tumor tissue was greatly increased.

From the results above, it was identified that the fusion polypeptide of the present invention increases the influx of the NK cells, an immunocyte therapeutic agent, thereby showing a remarkable effect on cancer treatment.

Figure 30A:
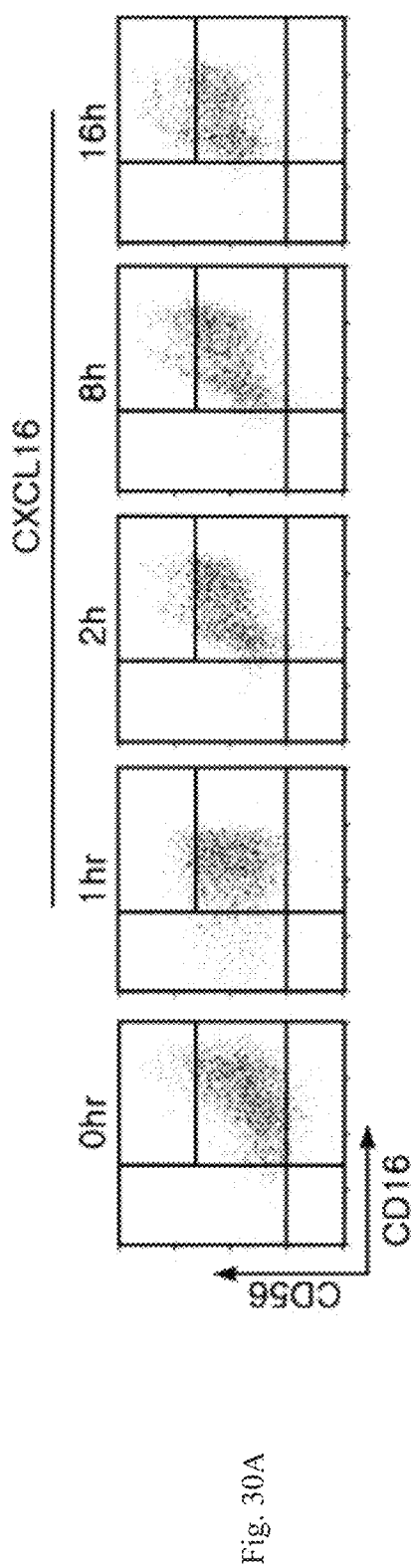
FIG. 30A is a diagram showing results of identifying a change in distribution of cells from $CD56^{dim}$ to $CD56^{bright}$ by means of CXCL16 treatment according to an elapse of time.
Figure 30B:
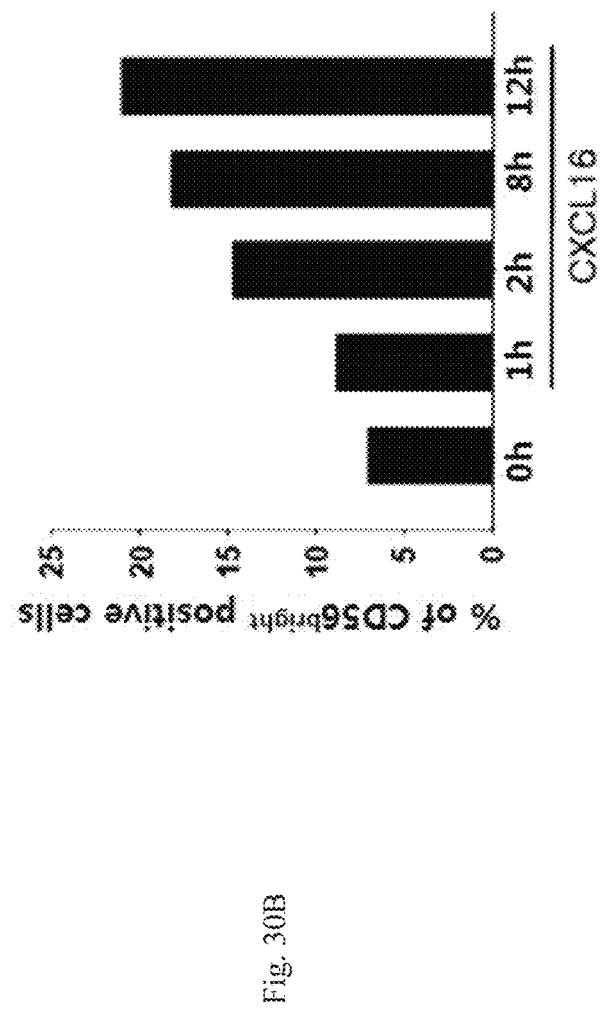
FIG. 30B is a graph showing quantification of $CD56^{bright}$ cells (%) over time.

<Example 9> Identification of a Characteristic Change of NK Cells According to CXCL16 Treatment To identify a characteristic change in the NK cells by means of CXCL16 released from the fusion polypeptide, the NK cells were treated with IL-2 and CXCL16, which promote a growth of the NK cells, at a concentration of 200 U and 100 nM respectively for 0, 1, 2, 8 or 16 hours, and a distribution of $CD56^{dim}$ and $CD56^{bright}$ was identified through the FACS, wherein the results thereof were shown in FIG. 30 and the cells in a square at the top right indicate $CD56^{bright}$ cells.

As identified in FIG. 30, it was identified that a distribution of cells were changed from $CD56^{dim}$ to $CD56^{bright}$ by means of CXCL16 treatment according to an elapse of time.

Also, the treatment with IL-2 and CXCL16 was simultaneously performed for a long period of time (14 days) in a similar way to the experimental method above, after which a change in CD56 expression was identified, wherein the results thereof were shown in FIG. 31.

Figure 31A:
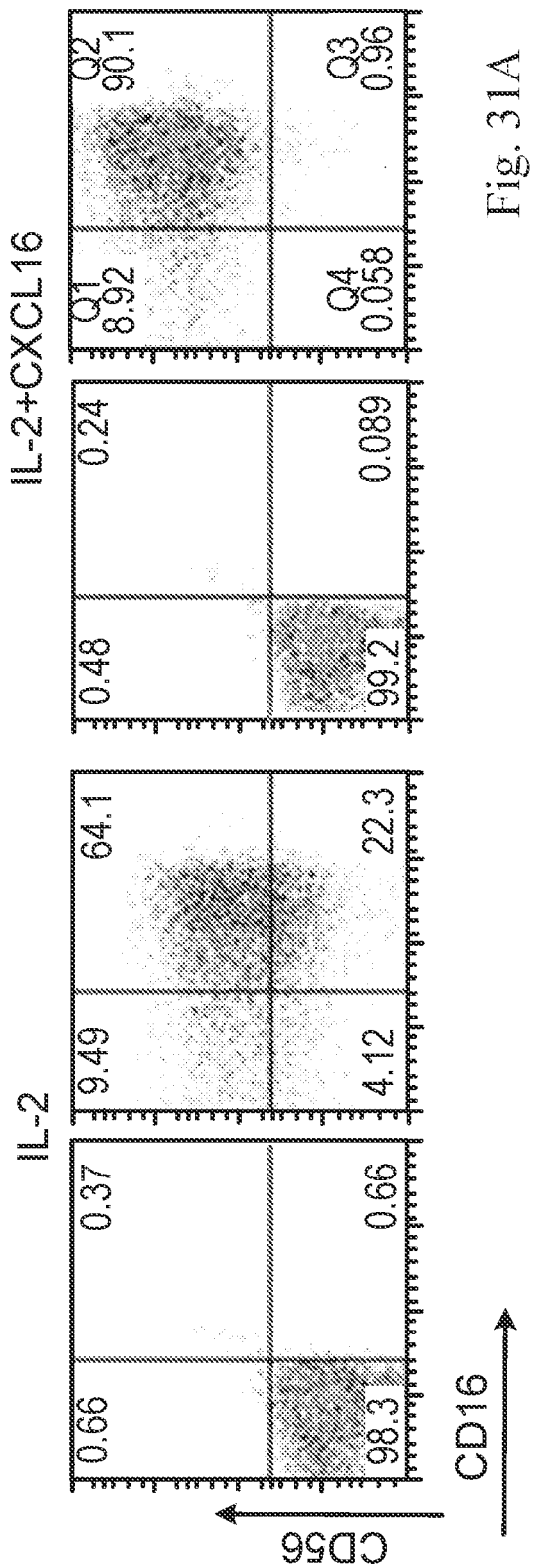
FIG. 31A is a diagram showing results of identifying a change in distribution of NK cells upon treatment with IL-2 and IL-2+CXCL16.
Figure 31B:
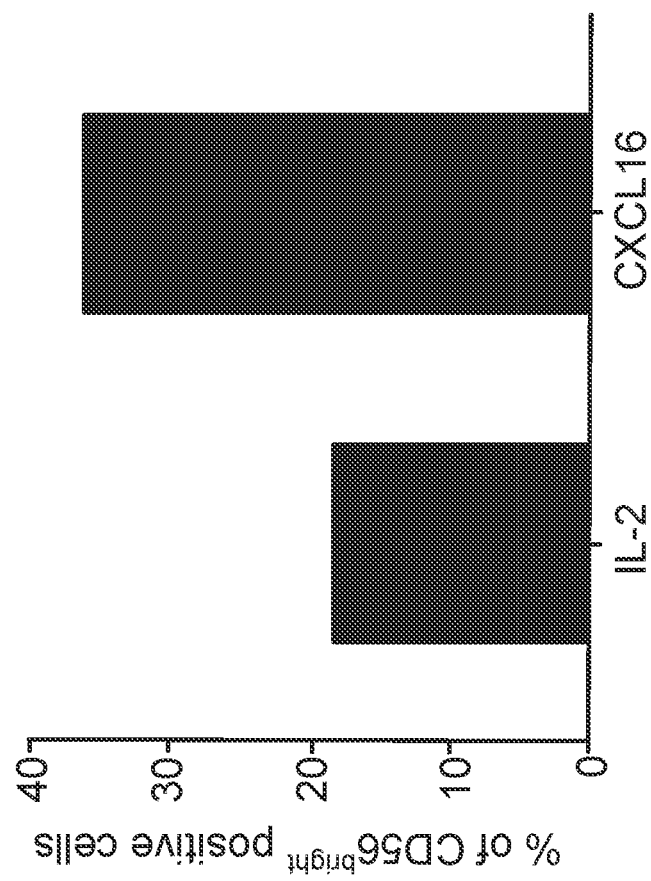
FIG. 31B is a graph showing quantification of $CD56^{bright}$ cells (%) over time in the IL-2 and CXCL16 treated groups.

As identified in FIG. 31, a change into $CD56^{bright}$ cells was identified in an experimental group dosed with IL2 and CXCL16 together (IL-2+CXCL16 of FIG. 31A and CXCL16 of FIG. 31B).

From the results above, it was identified that CXCL16 changes $CD56^{dim}$ into $CD56^{bright}$ having a large ADCC effect, thereby having an influence on characteristics of the NK cells.

<Example 10> Characteristic Change of NK Cells According to Treatment with the Fusion Polypeptide (NRP-Body)

It was identified about a change in an efficacy of the ADCC, which induced a death of cancer cells according to a distribution of the NK cells changed by means of CXCL16.

Panc-1 cell lines were divided by $2\times10^5$ into a 96-well plate, and cultured in a $CO_2$ incubator at 37° C. for two hours. The NK cells were added thereto by $2\times10^5$ to set a ratio of target cell and effector cell at 1:1, and cultured in the $CO_2$ incubator at 37° C. for four hours. The cells were collected therefrom, then washed with PBS, then stained with Annexin V (1 µg/ml) and PI (1 µg/ml) for 30 minutes, and then analyzed with the FACS.

Figure 32:
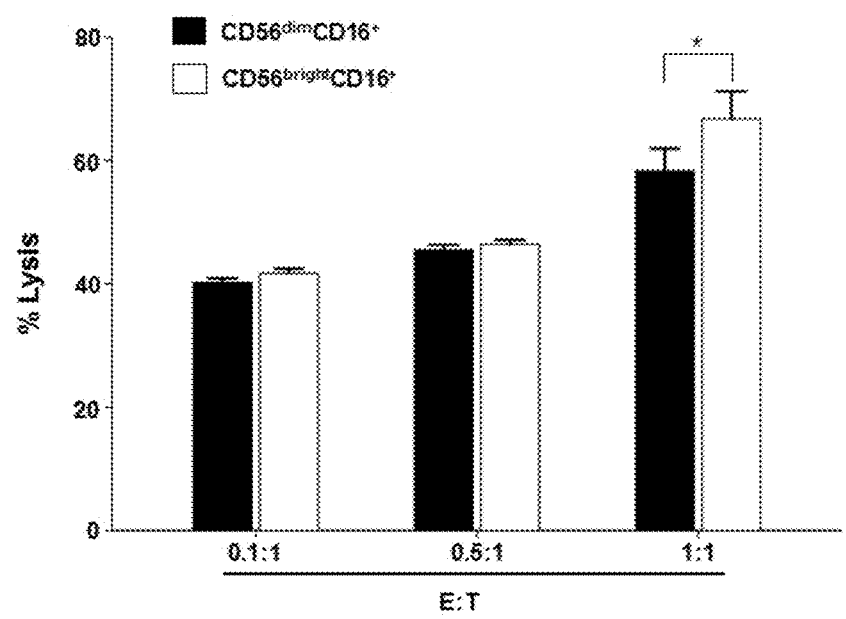
FIG. 32 is a graph of showing results of identifying an increase in cell deaths by means of $CD56^{bright}CD16^{+}$ NK cells, which are distributed upon treatment of the NK cells with the fusion polypeptide prepared according to the present invention.

The results thereof were shown in FIG. 32.

As identified in FIG. 32, it was identified that the death of cancer cells is increased by means of $CD56^{bright}$ $CD16^+$ NK cells, which are increased by CXCL16 of the fusion polypeptide.

The invention claimed is:

1. A fusion polypeptide, consisting of:
   an antibody or fragment thereof that binds to a tumor-associated antigen;
   a linker comprising a furin cleavage site; and
   a natural killer (NK) cell-inducing protein of CXCL16, wherein the CXCL16 consists of the amino acid sequence of SEQ ID NO: 17.

2. The fusion polypeptide, according to claim 1, wherein the tumor-associated antigen is at least one selected from the group consisting of mesothelin, PD-L1 (programmed death-ligand 1), Her2 (human EGFR-related 2), CD19, MUC1, EGFR, VEGFR, B7H1, B7H2, B7H3, BT-062, BTLA, CAIX, 4-1BB, 5T4, AGS-5 and AGS-16.

3. The fusion polypeptide, according to claim 1, wherein the antibody is a single-chain Fv fragment (scFv).

4. The fusion polypeptide, according to claim 1, wherein the furin cleavage site comprises the amino acid sequence of SEQ ID NO: 15.

5. A nucleic acid, coding the fusion polypeptide according to claim 1.

6. An expression vector, comprising the nucleic acid coding the fusion polypeptide according to claim 5.

7. A host cell, comprising the expression vector according to claim 6.

8. The host cell, according to claim 7, wherein the host cell is one selected from the group consisting of COS, CHO, HeLa and myeloma cell lines.

9. A pharmaceutical composition for preventing or treating a cancer, comprising a fusion polypeptide, wherein the fusion polypeptide consists of:
   an antibody or fragment thereof that binds to a tumor-associated antigen;
   a linker comprising a furin cleavage site; and
   a NK cell-inducing protein of CXCL16,
   wherein the CXCL16 consists of the amino acid sequence of SEQ ID NO: 17.

10. The pharmaceutical composition for preventing or treating cancer, according to claim 9, wherein the tumor-associated antigen is at least one selected from the group consisting of mesothelin, PD-L1, Her2, CD19, MUC1, EGFR, VEGFR, B7H1, B7H2, B7H3, BT-062, BTLA, CAIX, 4-1BB, 5T4, AGS-5 and AGS-16.

11. The pharmaceutical composition for preventing or treating a cancer, according to claim 9, wherein the cancer is one selected from the group consisting of pancreatic cancer, breast cancer, prostate cancer, gastric cancer, liver cancer or lung cancer.

12. A pharmaceutical composition for preventing or treating cancer, comprising a fusion polypeptide, wherein the fusion polypeptide consists of:
   an antibody or fragment thereof that binds to a tumor-associated antigen; a linker comprising a furin cleavage site; and a NK cell-inducing protein of CXCL16, and Natural killer cells,
   wherein the CXCL16 consists of the amino acid sequence of SEQ ID NO: 17.

13. A method of preventing or treating a cancer comprising administering to a subject an effective amount of fusion polypeptide, wherein the fusion polypeptide consists of:
   an antibody or fragment thereof that binds to a tumor-associated antigen;
   a linker comprising a furin cleavage site; and
   a NK cell-inducing protein of CXCL16,
   wherein the CXCL16 consists of the amino acid sequence of SEQ ID NO: 17.

* * * * *

SEQUENCE LISTING

<160> NUMBER OF SEQ ID NOS: 43

<210> SEQ ID NO 1
<211> LENGTH: 242
<212> TYPE: PRT
<213> ORGANISM: Artificial Sequence
<220> FEATURE:

<223> OTHER INFORMATION: Mesothelin scFV

<400> SEQUENCE: 1

Met Gln Val Gln Leu Gln Gln Ser Gly Pro Glu Leu Glu Lys Pro Gly
1               5                   10                  15

Ala Ser Val Lys Ile Ser Cys Lys Ala Ser Gly Tyr Ser Phe Thr Gly
            20                  25                  30

Tyr Thr Met Asn Trp Val Lys Gln Ser His Gly Lys Ser Leu Glu Trp
        35                  40                  45

Ile Gly Leu Ile Thr Pro Tyr Asn Gly Ala Ser Ser Tyr Asn Gln Lys
    50                  55                  60

Phe Arg Gly Lys Ala Thr Leu Thr Val Asp Lys Ser Ser Ser Thr Ala
65                  70                  75                  80

Tyr Met Asp Leu Leu Ser Leu Thr Ser Glu Asp Ser Ala Val Tyr Phe
                85                  90                  95

Cys Ala Arg Gly Gly Tyr Asp Gly Arg Gly Phe Asp Tyr Trp Gly Gln
            100                 105                 110

Gly Thr Thr Val Thr Val Ser Ser Gly Val Gly Gly Ser Gly Gly Gly
        115                 120                 125

Gly Ser Gly Gly Gly Ser Asp Ile Glu Leu Thr Gln Ser Pro Ala
    130                 135                 140

Ile Met Ser Ala Ser Pro Gly Glu Lys Val Thr Met Thr Cys Ser Ala
145                 150                 155                 160

Ser Ser Ser Val Ser Tyr Met His Trp Tyr Gln Gln Lys Ser Gly Thr
                165                 170                 175

Ser Pro Lys Arg Trp Ile Tyr Asp Thr Ser Lys Leu Ala Ser Gly Val
            180                 185                 190

Pro Gly Arg Phe Ser Gly Ser Gly Ser Gly Asn Ser Tyr Ser Leu Thr
        195                 200                 205

Ile Ser Ser Val Glu Glu Ala Glu Asp Asp Ala Thr Tyr Tyr Cys Gln
    210                 215                 220

Gln Trp Ser Gly Tyr Pro Leu Thr Phe Gly Ala Gly Thr Lys Leu Glu
225                 230                 235                 240

Ile Lys

<210> SEQ ID NO 2
<211> LENGTH: 723
<212> TYPE: DNA
<213> ORGANISM: Artificial Sequence
<220> FEATURE:
<223> OTHER INFORMATION: Mesothelin scFV

<400> SEQUENCE: 2
atgcaggtac aactgcagca gtctgggcct gagctggaga agcctggcgc ttcagtgaag      60
atatcctgca aggcttctgg ttactcattc actggctaca ccatgaactg ggtgaagcag     120
agccatggaa agagccttga gtggattgga cttattactc cttacaatgg tgcttctagc     180
tacaaccaga agttcagggg caaggccaca ttaactgtag acaagtcatc cagcacagcc     240
tacatggacc tcctcagtct gacatctgaa gactctgcag tctatttctg tgcaaggggg     300
ggttacgacg gagggggttt tgactactgg ggccaaggga ccacggtcac cgtctcctca     360
ggtgtaggcg gttcaggcgg cggtggctct ggcggtggcg gatcggacat cgagctcact     420
cagtctccag caatcatgtc tgcatctcca ggggagaagg tcaccatgac ctgcagtgcc     480
agctcaagtg taagttacat gcactggtac cagcagaagt caggcacctc ccccaaaaga     540

```
tggatttatg acacatccaa actggcttct ggagtcccag gtcgcttcag tggcagtggg      600
tctggaaact cttactctct cacaatcagc agcgtggagg ctgaagatga tgcaacttat      660
tactgccagc agtggagtgg ttaccctctc acgttcggtg ctgggacaaa gttggaaata      720
aaa                                                                    723
```

```
<210> SEQ ID NO 3
<211> LENGTH: 118
<212> TYPE: PRT
<213> ORGANISM: Artificial Sequence
<220> FEATURE:
<223> OTHER INFORMATION: PD-L1 scFv heavy chain

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Val His Trp Val Arg Gln Ala Pro Gly Gln Arg Leu Glu Trp Met
        35                  40                  45

Gly Trp Leu His Ala Asp Thr Gly Ile Thr Lys Phe Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Ile Gln Leu Trp Phe Asp Tyr Trp Gly Gln Gly Thr
            100                 105                 110

Leu Val Thr Val Ser Ser
        115
```

```
<210> SEQ ID NO 4
<211> LENGTH: 354
<212> TYPE: DNA
<213> ORGANISM: Artificial Sequence
<220> FEATURE:
<223> OTHER INFORMATION: PD-L1 scFv heavy chain

<400> SEQUENCE: 4
caggtccaac ttgtgcagtc tggggctgag gtgaagaagc ctggggcctc agtgaaggtt       60
tcctgcaagg cttctggata caccttcact agctatgatg tacattgggt gcgccaggcc      120
cccggacaaa ggcttgagtg gatgggatgg ctccacgctg acactggtat cacaaaattt      180
tcacagaagt tccagggcag agtcaccatt accagggaca catccgcgag cacagcctac      240
atggagctga gcagcctgag atctgaagac acggctgtgt attactgtgc gagggagagg      300
atacagctat ggtttgacta ctgggggccag ggaaccctgg tcaccgtctc ctca           354
```

```
<210> SEQ ID NO 5
<211> LENGTH: 107
<212> TYPE: PRT
<213> ORGANISM: Artificial Sequence
<220> FEATURE:
<223> OTHER INFORMATION: PD-L1 scFv light chain

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30
```

```
Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 6
<211> LENGTH: 321
<212> TYPE: DNA
<213> ORGANISM: Artificial Sequence
<220> FEATURE:
<223> OTHER INFORMATION: PD-L1 scFv light chain

<400> SEQUENCE: 6
gacatccaga tgacccagtc tccatcctca ctgtctgcat ctgtaggaga cagagtcacc      60
atcacttgtc gggcgagtca gggtattagc agctggttag cctggtatca gcagaaacca     120
gagaaagccc ctaagtccct gatctatgct gcatccagtt tgcaaagtgg ggtcccatca     180
aggttcagcg gcagtggatc tgggacagat ttcactctca ccatcagcag cctgcagcct     240
gaagattttg caacttatta ctgccaacag tataatagtt acccgtacac ttttggccag     300
gggaccaagc tggagatcaa a                                                321

<210> SEQ ID NO 7
<211> LENGTH: 1353
<212> TYPE: DNA
<213> ORGANISM: Artificial Sequence
<220> FEATURE:
<223> OTHER INFORMATION: PD-L1

<400> SEQUENCE: 7
aacataaccg gacagagcca ccaccctaca ggtcttcctc agagatcagc ttctgctcga      60
attccacgag gctggctcct ccacgcagca cggtcacttt tgtgccggtg ccgaacactc     120
tggtgctgct gcttgtgtag ctgctgcagt agtagtcggc ctcgtcctcg gcctgcagtc     180
cgctgatggt caggctggcg gtgttgccgc tcttgctgcc gctgaatctg ttggacacgc     240
cgctgggccg gttggacacg tcgtagatca tcagcttggg ggccttgccg gggtgctgct     300
gataccagga cacgtagttg tagccgccca cgtcgctgct ggtgcctgtg cagctgatgg     360
tgatgctctg gccagggctg ccggacacgc tggcaggctg tgtcagggcg ctctgggaac     420
ccacaccgct ggatccaccg gagcctcctc cgccactacc tcctcctccg aggcccccga     480
ggccagagga cacggtgacc agggtgccct ggccccagta gtccacggtg gtcacggtgc     540
ccagcttgat ccgggcgcag tagtacacgg cggtgtcctc ggcccgcagg ctgttcatct     600
gcaggtacag ggtgttcttg ctgttgtccc ggctgatggt gaaccggccc ttcacggtgt     660
cggcgtagaa ggtgatgccg ccgctggggt agatgctgga cacccattcc aggcccttgc     720
caggggcctg tcggacccac atcatgatat agctgctgaa tgtgaagccg ctggcggcgc     780
aagacagtct caggctgccg ccaggctgca ccagtcctcc gccgctttcc agcagctgca     840
cctcggccat ggccgctgg gccgcgagta ataacaatcc agcggctgcc gtaggcaata     900
ggtatttcat gatttgccct cgttatctag aaattcgtaa tcatggtcat agctgtttcc     960
```

```
tgtgtgaaat tgttatccgc tcacaattcc acacaacata cgagccggaa gcataaagtg        1020
taaagcctgg ggtgcctaat gagtgagcta actcacatta attgcgttga ggtgggctgc        1080
aaaacaaaac ggcctcctgt caggaagccg cttttatcgg gtaccgctca ctggccgctt        1140
tccagtcggg aaacctgtct tgccagctgc attaatgaat cggccaaccc ccggggaaaa        1200
ggcggttttc gttttggggg cccagggggg tttttttttt tccccgggga acggggggaca        1260 acctgatatg ccctttaccg cctgggcccc ggaaaaaatt taaaaaaagg ggccaccccct       1320 ggtttgcccc acaagggaaa aaacttgtgt ttg                                      1353

<210> SEQ ID NO 8
<211> LENGTH: 120
<212> TYPE: PRT
<213> ORGANISM: Artificial Sequence
<220> FEATURE:
<223> OTHER INFORMATION: Her2 scFv heavy chain

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Asx Tyr Tyr Cys
                85                  90                  95

Ser Arg Trp Gly Gly Asp Gly Phe Tyr Ala Met Asp Val Trp Gly Gln
            100                 105                 110

Gly Thr Leu Val Thr Val Ser Ser
        115                 120

<210> SEQ ID NO 9
<211> LENGTH: 363
<212> TYPE: DNA
<213> ORGANISM: Artificial Sequence
<220> FEATURE:
<223> OTHER INFORMATION: Her2 scFv heavy chain

<400> SEQUENCE: 9
atggaggttc agctggtgga gtctggcggt ggcctggtgc agccagggg ctcactccgt          60 ttgtcctgtg cagcttctgg cttcaacatt aaagacacct atatactgg gtgcgtcag          120 gccccgggta agggcctgga atgggttgca aggatttatc ctacgaatgg ttatactaga        180
tatgccgata gcgtcaaggg ccgtttcact ataagcgcag acacatccaa aaacacagcc        240
tacctgcaga tgaacagcct gcgtgctgag gacactgccg tctattattg ttctagatgg        300
ggaggggacg gcttctatgc tatggacgtg tggggtcaag aaccctggt caccgtctcc        360 tcg                                                                      363

<210> SEQ ID NO 10
<211> LENGTH: 107
<212> TYPE: PRT
<213> ORGANISM: Artificial Sequence
<220> FEATURE:
```

<223> OTHER INFORMATION: Her2 scFv light chain

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Glu Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 11
<211> LENGTH: 321
<212> TYPE: DNA
<213> ORGANISM: Artificial Sequence
<220> FEATURE:
<223> OTHER INFORMATION: Her2 scFv light chain

<400> SEQUENCE: 11
gatatccaga tgacccagtc cccgagctcc ctgtccgcct ctgtgggcga tagggtcacc      60
atcacctgcc gtgccagtca ggatgtgaat actgctgtag cctggtatca acagaaacca     120
ggaaaagctc cgaaactact gatttactcg gcatccttcc tcgagtctgg agtcccttct     180
cgcttctctg gatccagatc tgggacggat ttcactctga ccatcagcag tctgcagccg     240
gaagacttcg caacttatta ctgtcagcaa cattatacta ctcctcccac gttcggacag     300
ggtaccaagg tggagatcaa a                                               321

<210> SEQ ID NO 12
<211> LENGTH: 3768
<212> TYPE: DNA
<213> ORGANISM: Artificial Sequence
<220> FEATURE:
<223> OTHER INFORMATION: Her2

<400> SEQUENCE: 12
atggagctgg cggccttgtg ccgctggggg ctcctcctcg ccctcttgcc ccccggagcc      60
gcgagcaccc aagtgtgcac cggcacagac atgaagctgc ggctccctgc cagtcccgag     120
acccacctgg acatgctccg ccacctctac cagggctgcc aggtggtgca gggaaacctg     180
gaactcacct acctgcccac caatgccagc ctgtccttcc tgcaggatat ccaggaggtg     240
cagggctacg tgctcatcgc tcacaaccaa gtgaggcagg tcccactgca gaggctgcgg     300
attgtgcgag gcacccagct ctttgaggac aactatgccc tggccgtgct agacaatgga     360
gacccgctga acaataccac ccctgtcaca ggggcctccc caggaggcct gcgggagctg     420
cagcttcgaa gcctcacaga gatcttgaaa ggaggggtct tgatccagcg gaaccccag      480 ctctgctacc aggacacgat tttgtggaag gacatcttcc acaagaacaa ccagctggct     540
ctcacactga tagacaccaa ccgctctcgg gcctgccacc cctgttctcc gatgtgtaag     600
ggctcccgct gctgggggga gagttctgag gattgtcaga gcctgacgcg cactgtctgt     660

```
gccggtggct gtgcccgctg caaggggcca ctgcccactg actgctgcca tgagcagtgt    720
gctgccggct gcacgggccc caagcactct gactgcctgg cctgcctcca cttcaaccac    780
agtggcatct gtgagctgca ctgcccagcc ctggtcacct acaacacaga cacgtttgag    840
tccatgccca atcccgaggg ccggtataca ttcggcgcca gctgtgtgac tgcctgtccc    900
tacaactacc tttctacgga cgtgggatcc tgcaccctcg tctgccccct gcacaaccaa    960
gaggtgacag cagaggatgg aacacagcgg tgtgagaagt gcagcaagcc ctgtgcccga   1020
gtgtgctatg gtctgggcat ggagcacttg cgagaggtga gggcagttac cagtgccaat   1080
atccaggagt ttgctggctg caagaagatc tttgggagcc tggcatttct gccggagagc   1140
tttgatgggg acccagcctc caacactgcc ccgctccagc cagagcagct ccaagtgttt   1200
gagactctgg aagagatcac aggttaccta tacatctcag catggccgga cagcctgcct   1260
gacctcagcg tcttccagaa cctgcaagta atccggggac gaattctgca caatggcgcc   1320
tactcgctga ccctgcaagg gctgggcatc agctggctgg gctgcgctc actgagggaa   1380 ctgggcagtg gactggccct catccaccat aacacccacc tctgcttcgt gcacacggtg   1440
ccctgggacc agctctttcg gaacccgcac caagctctgc tccacactgc caaccggcca   1500
gaggacgagt gtgtgggcga gggcctggcc tgccaccagc tgtgcgcccg agggcactgc   1560
tggggtccag ggcccaccca gtgtgtcaac tgcagccagt tccttcgggg ccaggagtgc   1620
gtggaggaat gccgagtact gcaggggctc ccagggagt atgtgaatgc caggcactgt   1680
ttgccgtgcc accctgagtg tcagccccag aatggctcag tgacctgttt tggaccggag   1740
gctgaccagt gtgtggcctg tgcccactat aaggaccctc ccttctgcgt ggcccgctgc   1800
cccagcggtg tgaaacctga cctctcctac atgcccatct ggaagtttcc agatgaggag   1860
ggcgcatgcc agccttgccc catcaactgc acccactcct gtgtggacct ggatgacaag   1920
ggctgccccg ccgagcagag agccagccct ctgacgtcca tcgtctctgc ggtggttggc   1980
attctgctgg tcgtggtctt gggggtggtc tttgggatcc tcatcaagcg acggcagcag   2040
aagatccgga gtacacgat gcggagactg ctgcaggaaa cggagctggt ggagccgctg   2100
acacctagcg gagcgatgcc caaccaggcg cagatgcgga tcctgaaaga gacggagctg   2160
aggaaggtga aggtgcttgg atctggcgct tttggcacag tctacaaggg catctggatc   2220
cctgatgggg agaatgtgaa aattccagtg gccatcaaag tgttgaggga aaacacatcc   2280
cccaaagcca acaaagaaat cttagacgaa gcatacgtga tggctggtgt gggctcccca   2340
tatgtctccc gccttctggg catctgcctg acatccacgg tgcagctggt gacacagctt   2400
atgccctatg gctgcctctt agaccatgtc cgggaaaacc gcggacgcct gggctcccag   2460
gacctgctga actggtgtat gcagattgcc aaggggatga gctacctgga ggatgtgcgg   2520
ctcgtacaca gggacttggc cgctcggaac gtgctggtca gagtcccaa ccatgtcaaa   2580 attacagact cgggctggcc tcggctgctg acattgacg agacagagta ccatgcagat   2640
gggggcaagg tgcccatcaa gtggatggcg ctggagtcca ttctccgccg gcggttcacc   2700
caccagagtg atgtgtggag ttatggtgtg actgtgtggg agctgatgac ttttggggcc   2760
aaaccttacg atgggatccc agcccggag atccctgacc tgctggaaaa ggggagcgg   2820 ctgccccagc cccccatctg caccattgat gtctacatga tcatggtcaa atgttggatg   2880
attgactctg aatgtcggcc aagattccgg gagttggtgt ctgaattctc ccgcatggcc   2940 agggacccc agcgctttgt ggtcatccag aatgaggact gggcccagc cagtcccttg   3000 gacagcacct tctaccgctc actgctggag gacgatgaca tggggacct ggtggatgct   3060
```

```
gaggagtatc tggtacccca gcagggcttc ttctgtccag accctgcccc gggcgctggg   3120
ggcatggtcc accacaggca ccgcagctca tctaccagga gtggcggtgg ggacctgaca   3180
ctagggctgg agccctctga agaggaggcc cccaggtctc cactggcacc ctccgaaggg   3240
gctggctccg atgtatttga tggtgacctg ggaatggggg cagccaaggg gctgcaaagc   3300
ctccccacac atgaccccag ccctctacag cggtacagtg aggaccccac agtaccccdg   3360
ccctctgaga ctgatggcta cgttgccccc ctgacctgca gccccagcc tgaatatgtg    3420 aaccagccag atgttcggcc ccagccccct tcgccccgag agggccctct gcctgctgcc   3480
cgacctgctg gtgccactct ggaaagggcc aagactctct ccccagggaa gaatggggtc   3540
gtcaaagacg ttttgccttt tgggggtgcc gtggagaacc ccgagtactt gacacccccag  3600 ggaggagctg cccctcagcc ccaccctcct cctgccttca gcccagcctt cgacaacctc   3660
tattactggg accaggaccc accagagcgg ggggctccac ccagcacctt caaagggaca   3720
cctacggcag agaacccaga gtacctgggt ctggacgtgc cagtgtga              3768
```

<210> SEQ ID NO 13
<211> LENGTH: 235
<212> TYPE: PRT
<213> ORGANISM: Artificial Sequence
<220> FEATURE:
<223> OTHER INFORMATION: FC

<400> SEQUENCE: 13

```
Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Phe Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Ile Leu Gln Ile Ser Ile Thr Leu
225                 230                 235
```

```
<210> SEQ ID NO 14
<211> LENGTH: 705
<212> TYPE: DNA
<213> ORGANISM: Artificial Sequence
<220> FEATURE:
<223> OTHER INFORMATION: FC

<400> SEQUENCE: 14
gacaaaactc acacatgccc accgtgccca gcacctgaac tcctgggggg accgtcagtc      60
ttcctcttcc ccccaaaacc caaggacacc ctcatgatct cccggacccc tgaggtcaca     120
tgcgtggtgg tggacgtgag ccacgaagac cctgaggtca agttcaactg gtacgtggac     180
ggcgtggagg tgcataatgc caagacaaag ccgcgggagg agcagtacaa cagcacgtac     240
cgtgtggtca gcgtcctcac cgtcctgcac caggactggc tgaatggcaa ggagtacaag     300
tgcaaggtct ccaacaaagc cctcccagcc cccatcgaga aaaccatctc caaagccaaa     360
gggcagcccc gagaaccaca ggtgtacacc ctgcccccat cccgggatga gctgaccaag     420
aaccaggtca gcctgacctg cctggtcaaa ggcttctatc ccagcgacat cgccgtggag     480
tgggagagca atgggcagcc ggagaacaac tacaagacca cgcctcccgt gctggactcc     540
gacggctcct tcttcttcta cagcaagctc accgtggaca agagcaggtg gcagcagggg     600
aacgtcttct catgctccgt gatgcatgag gctctgcaca accactacac gcagaagagc     660
ctctccctgt ctccgggtaa aattctgcag atatccatca cactg                    705

<210> SEQ ID NO 15
<211> LENGTH: 4
<212> TYPE: PRT
<213> ORGANISM: Artificial Sequence
<220> FEATURE:
<223> OTHER INFORMATION: Furin

<400> SEQUENCE: 15

Arg Val Lys Arg
1

<210> SEQ ID NO 16
<211> LENGTH: 13
<212> TYPE: DNA
<213> ORGANISM: Artificial Sequence
<220> FEATURE:
<223> OTHER INFORMATION: Furin

<400> SEQUENCE: 16
acgggtgaag cgg                                                         13

<210> SEQ ID NO 17
<211> LENGTH: 89
<212> TYPE: PRT
<213> ORGANISM: Artificial Sequence
<220> FEATURE:
<223> OTHER INFORMATION: CXCL16

<400> SEQUENCE: 17

Asn Glu Gly Ser Val Thr Gly Ser Cys Tyr Cys Gly Lys Arg Ile Ser
1               5                   10                  15

Ser Asp Ser Pro Pro Ser Val Gln Phe Met Asn Arg Leu Arg Lys His
            20                  25                  30

Leu Arg Ala Tyr His Arg Cys Leu Tyr Tyr Thr Arg Phe Gln Leu Leu
        35                  40                  45
```

Ser Trp Ser Val Cys Gly Gly Asn Lys Asp Pro Trp Val Gln Glu Leu
         50                  55                  60

Met Ser Cys Leu Asp Leu Lys Glu Cys Gly His Ala Tyr Ser Gly Ile
65                  70                  75                  80

Val Ala His Gln Lys His Leu Leu Pro
                85

<210> SEQ ID NO 18
<211> LENGTH: 270
<212> TYPE: DNA
<213> ORGANISM: Artificial Sequence
<220> FEATURE:
<223> OTHER INFORMATION: CXCL16

<400> SEQUENCE: 18
aacgagggca gcgtcactgg aagttgttat tgtggtaaaa gaatttcttc cgactccccg     60
ccatcggttc agttcatgaa tcgtctccgg aaacacctga gcttacca tcggtgtcta    120 tactacacga ggttccagct cctttcctgg agcgtgtgtg gaggcaacaa ggacccatgg    180
gttcaggaat tgatgagctg tcttgatctc aaagaatgtg gacatgctta ctcggggatt    240
gtggcccacc agaagcattt acttccttag                                     270

<210> SEQ ID NO 19
<211> LENGTH: 8748
<212> TYPE: DNA
<213> ORGANISM: Artificial Sequence
<220> FEATURE:
<223> OTHER INFORMATION: Fusion protein expression vector

<400> SEQUENCE: 19
gacggatcgg gagatctccc gatccctat ggtcgactct cagtacaatc tgctctgatg      60
ccgcatagtt aagccagtat ctgctccctg cttgtgtgtt ggaggtcgct gagtagtgcg    120
cgagcaaaat ttaagctaca caaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttggtacc    900
gagctcggat ccatgggatg gagctatatc atcctctttt tggtagcaac agctacagat    960
gtccactcgg cccagccggc catggccgac caggtacaga tgcagctggt agagtctggg   1020
gctgaagtga agaagcctgg ggcttcagtg aagctgtcct gcaaggcttc tggctacacc   1080
ttcagcagct actggatgca ctgggtgcgc caggccctg acaacgcct gagtggatg    1140 ggagagatta tcctggcaa cggtcatact aactacaacg agaagttcaa gtcacgcgtg   1200

-continued

```
acaatcactg tagacaaatc cgcgagcaca gcctacatgg agctcagcag cctgagatct    1260
gagaacacgg cggtctatta ctgtgcaaga tcttttacta cggcacgggc gtttgcttac    1320
tggggccaag ggactctggt caccgtctcc tcaggcctcg gatgcaggta caactgcagc    1380
agtctgggcc tgagctggag aagcctggcg cttcagtgaa gatatcctgc aaggcttctg    1440
gttactcatt cactggctac accatgaact gggtgaagca gagccatgga agagccttg     1500 agtggattgg acttattact ccttacaatg gtgcttctag ctacaaccag aagttcaggg    1560
gcaaggccac attaactgta gacaagtcat ccagcacagc ctacatggac ctcctcagtc    1620
tgacatctga agactctgca gtctatttct gtgcaagggg gggttacgac gggaggggtt    1680
ttgactactg gggccaaggg accacggtca ccgtctcctc aggtgtaggc ggttcaggcg    1740
gcggtggctc tggcggtggc ggatcggaca tcgagctcac tcagtctcca gcaatcatgt    1800
ctgcatctcc aggggagaag gtcaccatga cctgcagtgc cagctcaagt gtaagttaca    1860
tgcactggta ccagcagaag tcaggcacct cccccaaaag atggatttat gacacatcca    1920
aactggcttc tggagtccca ggtcgcttca gtggcagtgg gtctgaaaac tcttactctc    1980
tcacaatcag cagcgtggag ctgaagatg atgcaactta ttactgccag cagtggagtg     2040
gttaccctct cacgttcggt gctgggacaa agttggaaat aaaagggccc atcggccggt    2100
gggccctggt ccgcgcggc agcgctagcg acaaaactca cacatgccca ccgtgcccag     2160
cacctgaact cctgggggga ccgtcagtct tcctcttccc cccaaaaccc aaggacaccc    2220
tcatgatctc ccggacccct gaggtcacat gcgtggtggt ggacgtgagc cacgaagacc    2280
ctgaggtcaa gttcaactgg tacgtggacg gcgtggaggg cataatgcc aagacaaagc     2340 ggcgggagga gcagtacaac agcacgtacc gtgtggtcag cgtcctcacc gtcctgcacc    2400
aggactggct gaatggcaag gagtacaagt gcaaggtctc caacaaagcc ctcccagccc    2460
ccatcgagaa aaccatctcc aaagccaaag gcagccccg agaaccacag gtgtacaccc     2520
tgcccccatc ccgggatgag ctgaccaaga accaggtcag cctgacctgc ctggtcaaag    2580
gcttctatcc cagcgacatc gccgtggagt gggagagcaa tgggcagccg gagaacaact    2640
acaagaccac gcctcccgtg ctggactccg acggctcctt cttcttctac agcaagctca    2700
ccgtggacaa gagcaggtgg cagcagggga acgtcttctc atgctccgtg atgcatgagg    2760
ctctgcacaa ccactacacg cagaagagcc tctccctgtc tccgggtaaa attctgcaga    2820
tatccatcac actggcggcc gcacgggtga agcggaacga gggcagcgtc actggaagtt    2880
gttattgtgg taaagaatt tcttccgact ccccgccatc ggttcagttc atgaatcgtc      2940
tccggaaaca cctgagagct taccatcggt gtctatacta cacgaggttc cagctccttt    3000
cctggagcgt gtgtggaggc aacaaggacc catgggttca ggaattgatg agctgtcttg    3060
atctcaaaga atgtggacat gcttactcgg ggattgtggc ccaccagaag catttacttc    3120
cttaggcggc cgctcgagat tccgcccctc tccctccccc cccctaacg ttactggccg      3180 aagccgcttg gaataaggcc ggtgtgcgtt tgtctatatg tgattttcca ccatattgcc    3240
gtcttttggc aatgtgaggg cccggaaacc tggccctgtc ttcttgacga gcattcctag    3300
gggtctttcc cctctcgcca aaggaatgca aggtctgttg aatgtcgtga aggaagcagt    3360
tcctctggaa gcttcttgaa gacaaacaac gtctgtagcg accctttgca ggcagcggaa    3420 cccccccacct ggcgacaggt gcctctgcgg ccaaaagcca cgtgtataag atacacctgc    3480
aaaggcggca caaccccagt gccacgttgt gagttggata ttgtggaaa gagtcaaatg      3540 gctctcctca agcgtattca acaagggct gaaggatgcc cagaaggtac cccattgtat     3600
```

```
gggatctgat ctggggcctc ggtgcacatg ctttacatgt gtttagtcga ggttaaaaaa    3660
acgtctaggc cccccgaacc acggggacgt ggttttcctt tgaaaaacat cgatgataat    3720
atggttcgac cattgaactg catcgtcgcc gtgtcccaaa atatggggat tggcaagaac    3780
ggagacctac cctggcctcc gctcaggaac gagttcaagt acttccaaag aatgaccaca    3840
acctcttcag tggaaggtaa acagaatctg gtgattatgg gtaggaaaac ctggttctcc    3900
attcctgaga agaatcgacc tttaaaggac agaatcaata tagttctcag tagagaactc    3960
aaagaaccac cacgaggagc tcattttctt gccaaaagtt tggatgatgc cttaagactt    4020
attgaacaac cggaattggc aagtaaagta gacatggttt ggatagtcgg aggcagttct    4080
gtttaccagg aagccatgaa tcaaccaggc cacctcagac tctttgtgac aaggatcatg    4140
caggaatttg aaagtgacac gttttttccca gaaattgatt tggggaaata taaacttctc    4200
ccagaatacc caggcgtcct ctctgaggtc caggaggaaa aaggcatcaa gtataagttt    4260
gaagtctacg agaagaaaga ctaatctaga gggccctatt ctatagtgtc acctaaatgc    4320
tagagctcgc tgatcagcct cgactgtgcc ttctagttgc cagccatctg ttgtttgccc    4380
ctcccccgtg ccttccttga ccctggaagg tgccactccc actgtccttt cctaataaaa    4440
tgaggaaatt gcatcgcatt gtctgagtag gtgtcattct attctggggg gtggggtggg    4500
gcaggacagc aagggggagg attgggaaga caatagcagg catgctgggg atgcggtggg    4560
ctctatggct tctgaggcgg aaagaaccag ctggggctct agggggtatc cccacgcgcc    4620
ctgtagcggc gcattaagcg cggcgggtgt ggtggttacg cgcagcgtga ccgctacact    4680
tgccagcgcc ctagcgcccg ctcctttcgc tttcttccct cctttctcg ccacgttcgc     4740 cggctttccc cgtcaagctc taaatcgggg catccctta gggttccgat ttagtgcttt     4800
acggcacctc gaccccaaaa aacttgatta gggtgatggt tcacgtagtg ggccatcgcc     4860
ctgatagacg ttttttcgcc ctttgacgtt ggagtccacg ttctttaata gtggactctt     4920
gttccaaact ggaacaacac tcaaccctat ctcggtctat tcttttgatt tataagggat     4980 tttgggggatt tcggcctatt ggttaaaaaa tgagctgatt taacaaaaat ttaacgcgaa    5040
ttaattctgt ggaatgtgtg tcagttaggg tgtggaaagt ccccaggctc cccaggcagg    5100
cagaagtatg caaagcatgc atctcaatta gtcagcaacc aggtgtggaa agtccccagg    5160
ctccccagca ggcagaagta tgcaaagcat gcatctcaat tagtcagcaa ccatagtccc    5220
gcccctaact ccgcccatcc cgcccctaac tccgcccagt tccgcccatt ctccgcccca    5280
tggctgacta attttttta tttatgcaga ggccgaggcc gcctctgcct ctgagctatt    5340
ccagaagtag tgaggaggct ttttggagg cctaggcttt tgcaaaaagc tcccgggagc     5400
ttgtatatcc attttcggat ctgatcaaga gacaggatga ggatcgtttc gcatgattga    5460
acaagatgga ttgcacgcag gttctccggc cgcttgggtg gagaggctat tcggctatga    5520
ctgggcacaa cagacaatcg gctgctctga tgccgccgtg ttccggctgt cagcgcaggg    5580
gcgcccggtt cttttttgtca agaccgacct gtccggtgcc ctgaatgaac tgcaggacga    5640
ggcagcgcgg ctatcgtggc tggccacgac gggcgttcct tgcgcagctg tgctcgacgt    5700
tgtcactgaa gcgggaaggg actggctgct attgggcgaa gtgccggggc aggatctcct    5760
gtcatctcac cttgctcctg ccgagaaagt atccatcatg gctgatgcaa tgcggcggct    5820
gcatacgctt gatccggcta cctgcccatt cgaccaccaa gcgaaacatc gcatcgagcg    5880
agcacgtact cggatggaag ccggtcttgt cgatcaggat gatctggacg aagagcatca    5940
```

```
ggggctcgcg ccagccgaac tgttcgccag gctcaaggcg cgcatgcccg acggcgagga      6000
tctcgtcgtg acccatggcg atgcctgctt gccgaatatc atggtggaaa atggccgctt      6060
ttctggattc atcgactgtg gccggctggg tgtggcggac cgctatcagg acatagcgtt      6120
ggctacccgt gatattgctg aagagcttgg cggcgaatgg gctgaccgct tcctcgtgct      6180
ttacggtatc gccgctcccg attcgcagcg catcgccttc tatcgccttc ttgacgagtt      6240
cttctgagcg ggactctggg gttcgaaatg accgaccaag cgacgcccaa cctgccatca      6300
cgagatttcg attccaccgc cgccttctat gaaaggttgg gcttcggaat cgttttccgg      6360
gacgccggct ggatgatcct ccagcgcggg gatctcatgc tggagttctt cgcccacccc      6420
aacttgttta ttgcagctta taatggttac aaataaagca atagcatcac aaatttcaca      6480
aataaagcat ttttttcact gcattctagt tgtggtttgt ccaaactcat caatgtatct      6540
tatcatgtct gtataccgtc gacctctagc tagagcttgg cgtaatcatg gtcatagctg      6600
tttcctgtgt gaaattgtta tccgctcaca attccacaca acatacgagc cggaagcata      6660
aagtgtaaag cctggggtgc ctaatgagtg agctaactca cattaattgc gttgcgctca      6720
ctgcccgctt tccagtcggg aaacctgtcg tgccagctgc attaatgaat cggccaacgc      6780
gcggggagag gcggtttgcg tattgggcgc tcttccgctt cctcgctcac tgactcgctg      6840
cgctcggtcg ttcggctgcg gcgagcggta tcagctcact caaaggcggt aatacggtta      6900
tccacagaat caggggataa cgcaggaaag aacatgtgag caaaaggcca gcaaaaggcc      6960
aggaaccgta aaaaggccgc gttgctggcg ttttttccata ggctccgccc ccctgacgag      7020
catcacaaaa atcgacgctc aagtcagagg tggcgaaacc cgacaggact ataaagatac      7080
caggcgtttc ccctggaag ctccctcgtg cgctctcctg ttccgaccct gccgcttacc      7140
ggatacctgt ccgcctttct cccttcggga agcgtggcgc tttctcaatg ctcacgctgt      7200
aggtatctca gttcggtgta ggtcgttcgc tccaagctgg gctgtgtgca cgaaccccc       7260 gttcagcccg accgctgcgc cttatccggt aactatcgtc ttgagtccaa cccggtaaga      7320
cacgacttat cgccactggc agcagccact ggtaacagga ttagcagagc gaggtatgta      7380
ggcggtgcta cagagttctt gaagtggtgg cctaactacg gctacactag aaggacagta      7440
tttggtatct gcgctctgct gaagccagtt accttcggaa aaagagttgg tagctcttga      7500
tccggcaaac aaaccaccgc tggtagcggt ggtttttttg tttgcaagca gcagattacg      7560
cgcagaaaaa aaggatctca agaagatcct ttgatctttt ctacggggtc tgacgctcag      7620
tggaacgaaa actcacgtta agggattttg gtcatgagat tatcaaaaag gatcttcacc      7680
tagatccttt taaattaaaa atgaagtttt aaatcaatct aaagtatata tgagtaaact      7740
tggtctgaca gttaccaatg cttaatcagt gaggcaccta tctcagcgat ctgtctattt      7800
cgttcatcca tagttgcctg actccccgtc gtgtagataa ctacgatacg ggagggctta      7860
ccatctggcc ccagtgctgc aatgataccg cgagacccac gctcaccggc tccagattta      7920
tcagcaataa accagccagc cggaagggcc gagcgcagaa gtggtcctgc aactttatcc      7980
gcctccatcc agtctattaa ttgttgccgg gaagctagag taagtagttc gccagttaat      8040
agtttgcgca acgttgttgc cattgctaca ggcatcgtgg tgtcacgctc gtcgtttggt      8100
atggcttcat tcagctccgg ttcccaacga tcaaggcgag ttacatgatc ccccatgttg      8160
tgcaaaaaag cggttagctc cttcggtcct ccgatcgttg tcagaagtaa gttggccgca      8220
gtgttatcac tcatggttat ggcagcactg cataattctc ttactgtcat gccatccgta      8280
agatgctttt ctgtgactgg tgagtactca accaagtcat tctgagaata gtgtatgcgg      8340
```

```
cgaccgagtt gctcttgccc ggcgtcaata cgggataata ccgcgccaca tagcagaact    8400
ttaaaagtgc tcatcattgg aaaacgttct tcggggcgaa aactctcaag gatcttaccg    8460
ctgttgagat ccagttcgat gtaacccact cgtgcaccca actgatcttc agcatctttt    8520
actttcacca gcgtttctgg gtgagcaaaa acaggaaggc aaaatgccgc aaaaaaggga    8580
ataagggcga cacggaaatg ttgaatactc atactcttcc ttttcaata ttattgaagc     8640 atttatcagg gttattgtct catgagcgga tacatatttg aatgtattta gaaaaataaa    8700
caaatagggg ttccgcgcac atttccccga aaagtgccac ctgacgtc                 8748
```

<210> SEQ ID NO 20
<211> LENGTH: 34
<212> TYPE: DNA
<213> ORGANISM: Artificial Sequence
<220> FEATURE:
<223> OTHER INFORMATION: Mesothelin scFv Forward primer

<400> SEQUENCE: 20
ggcccagccg gccatgcagg tacaactgca gcag                                34

<210> SEQ ID NO 21
<211> LENGTH: 39
<212> TYPE: DNA
<213> ORGANISM: Artificial Sequence
<220> FEATURE:
<223> OTHER INFORMATION: Mesothelin scFv Reverse primer

<400> SEQUENCE: 21
ggcccttggt ggaggcactc gagacggtga ccagggttc                           39

<210> SEQ ID NO 22
<211> LENGTH: 36
<212> TYPE: DNA
<213> ORGANISM: Artificial Sequence
<220> FEATURE:
<223> OTHER INFORMATION: PD-L1 scFv Forward primer

<400> SEQUENCE: 22
ggcccagccg gccatgcagg tccaacttgt gcagtc                              36

<210> SEQ ID NO 23
<211> LENGTH: 30
<212> TYPE: DNA
<213> ORGANISM: Artificial Sequence
<220> FEATURE:
<223> OTHER INFORMATION: PD-L1 scFv Reverse primer

<400> SEQUENCE: 23
ggcccttggt ggaccaagct ggagatcaaa                                     30

<210> SEQ ID NO 24
<211> LENGTH: 33
<212> TYPE: DNA
<213> ORGANISM: Artificial Sequence
<220> FEATURE:
<223> OTHER INFORMATION: Her2 scFv Forward primer

<400> SEQUENCE: 24
ggcccagccg gccatggagg ttcagctggt gga                                 33

<210> SEQ ID NO 25
<211> LENGTH: 28
<212> TYPE: DNA

```
<213> ORGANISM: Artificial Sequence
<220> FEATURE:
<223> OTHER INFORMATION: Her2 scFv Reverse primer

<400> SEQUENCE: 25
ggcccttggt accaaggtgg agatcaaa                                              28

<210> SEQ ID NO 26
<211> LENGTH: 39
<212> TYPE: DNA
<213> ORGANISM: Artificial Sequence
<220> FEATURE:
<223> OTHER INFORMATION: CXCL16, Furin cleavage site Forward primer

<400> SEQUENCE: 26
cacactggcg gccgcacggg tgaagcggaa cgagggcag                                  39

<210> SEQ ID NO 27
<211> LENGTH: 40
<212> TYPE: DNA
<213> ORGANISM: Artificial Sequence
<220> FEATURE:
<223> OTHER INFORMATION: CXCL16, Furin cleavage site Reverse primer

<400> SEQUENCE: 27
aatctcgagc ggccgcctaa ggaagtaaat gcttctggtg                                 40

<210> SEQ ID NO 28
<211> LENGTH: 119
<212> TYPE: PRT
<213> ORGANISM: Artificial Sequence
<220> FEATURE:
<223> OTHER INFORMATION: CD19 scFv heavy chain

<400> SEQUENCE: 28
```

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Glu Asp Thr Asn Tyr Ser Gly Lys Phe
    50                  55                  60

Lys Asp Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Arg Ser Leu Leu Tyr Gly Asp Tyr Leu Asp Tyr Trp Gly Gln Gly
            100                 105                 110

Thr Thr Leu Thr Val Ser Ser
        115

```
<210> SEQ ID NO 29
<211> LENGTH: 357
<212> TYPE: DNA
<213> ORGANISM: Artificial Sequence
<220> FEATURE:
<223> OTHER INFORMATION: CD19 scFv heavy chain

<400> SEQUENCE: 29
caggtgcagc tgcagcagag cggcccggaa ctggtgaaac cgggcgcgag cgtgaaaatt      60
agctgcaaag cgagcggcta tgcgtttagc agcagctgga tgaactgggt gaaacagcgc     120
```

```
ccgggcaaag gcctggaatg gattggccgc atttatccgg gcgatgaaga taccaactat    180
agcggcaaat ttaaagataa agcgaccctg accgcgata aaagcagcac caccgcgtat    240
atgcagctga gcagcctgac agcgaagat agcgcggtgt attttttgcgc gcgcagcctg    300 ctgtatggcg attatctgga ttattggggc agggcacca ccctgaccgt gagcagc       357
```

<210> SEQ ID NO 30
<211> LENGTH: 107
<212> TYPE: PRT
<213> ORGANISM: Artificial Sequence
<220> FEATURE:
<223> OTHER INFORMATION: CD19 scFv light chain

<400> SEQUENCE: 30

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Arg Phe Ser Gly Ser
    50                  55                  60

Gly Ser Gly Thr Ser Tyr Phe Leu Thr Ile Asn Asn Met Glu Ala Glu
65                  70                  75                  80

Asp Ala Ala Thr Tyr Tyr Cys Gln Gln Trp Asn Ile Asn Pro Leu Thr
                85                  90                  95

Phe Gly Ala Gly Thr Lys Leu Glu Leu Lys Arg
            100                 105
```

<210> SEQ ID NO 31
<211> LENGTH: 321
<212> TYPE: DNA
<213> ORGANISM: Artificial Sequence
<220> FEATURE:
<223> OTHER INFORMATION: CD19 scFv light chain

<400> SEQUENCE: 31

```
cagattgtgc tgacccagag cccggcgatt atgagcgcga gcccgggcga aaaagtgacc    60
atgacctgca gcgcgagcag cagcgtgagc tatatgcatt ggtatcagca gaaaagcggc   120
accagcccga acgctggat ttatgatacc agcaaactgg cgagcggcgt gccggatcgc    180
tttagcggca gcggcagcgg caccagctat tttctgacca ttaacaacat ggaagcggaa   240
gatgcggcga cctattattg ccagcagtgg aacattaacc cgctgacctt tggcgcgggc   300
accaaactgg aactgaaacg c                                              321
```

<210> SEQ ID NO 32
<211> LENGTH: 118
<212> TYPE: PRT
<213> ORGANISM: Artificial Sequence
<220> FEATURE:
<223> OTHER INFORMATION: MCU-1 scFv heavy chain

<400> SEQUENCE: 32

```
Gln Val Lys Leu Gln Gln Ser Gly Thr Glu Val Val Lys Pro Gly Ala
1               5                   10                  15

Ser Val Lys Leu Ser Cys Lys Ala Ser Gly Tyr Ile Phe Thr Ser Tyr
            20                  25                  30
```

Asp Ile Asp Trp Val Arg Gln Thr Pro Glu Gln Gly Leu Glu Trp Ile
            35                  40                  45

Gly Trp Ile Phe Pro Gly Glu Gly Ser Thr Glu Tyr Asn Glu Lys Phe
     50                  55                  60

Lys Gly Arg Ala Thr Leu Ser Val Asp Lys Ser Ser Thr Ala Tyr
 65                  70                  75                  80

Met Glu Leu Thr Arg Leu Thr Ser Glu Asp Ser Ala Val Tyr Phe Cys
                 85                  90                  95

Ala Arg Gly Asp Tyr Tyr Arg Arg Tyr Phe Asp Leu Trp Gly Gln Gly
             100                 105                 110

Thr Thr Val Thr Val Ser
            115

<210> SEQ ID NO 33
<211> LENGTH: 353
<212> TYPE: DNA
<213> ORGANISM: Artificial Sequence
<220> FEATURE:
<223> OTHER INFORMATION: MCU-1 scFv heavy chain

<400> SEQUENCE: 33
caggtgaaac tgcagcagag cggcaccgaa gtggtgaaac cgggcgcgag cgtgaaactg      60
agctgcaaag cgagcggcta tttttttacc agctatgata ttgattgggt gcgccagacc     120
ccggaacagg gcctggatgg attggctgga ttttttccggg cgaaggcagc accgaatata    180
acgaaaaatt taaggccgc gcgaccctga gcgtggataa aagcagcagc accgcgtata     240
tggaactgac ccgcctgacc agcgaagata gcgcggtgta tttttgcgcg cgcggcgatt    300
attatcgccg ctatttttgat ctgtggggcc agggcaccac cgtgaccgtg agc           353

<210> SEQ ID NO 34
<211> LENGTH: 109
<212> TYPE: PRT
<213> ORGANISM: Artificial Sequence
<220> FEATURE:
<223> OTHER INFORMATION: MCU-1 scFv light chain

<400> SEQUENCE: 34

Asp Ile Glu Leu Thr Gln Ser Pro Ala Ile Met Ser Ala Ser Pro Gly
 1               5                  10                  15

Glu Arg Val Thr Met Thr Cys Ser Ala Ser Ser Ser Ile Arg Tyr Ile
             20                  25                  30

Tyr Trp Tyr Gln Gln Lys Pro Gly Ser Ser Pro Arg Leu Leu Tyr Asp
         35                  40                  45

Thr Ser Asn Val Ala Pro Gly Val Pro Phe Arg Phe Ser Gly Ser Gly
     50                  55                  60

Ser Gly Thr Ser Tyr Ser Leu Thr Ile Asn Arg Met Glu Ala Glu Asp
 65                  70                  75                  80

Ala Ala Thr Tyr Tyr Cys Gln Glu Trp Ser Gly Tyr Pro Tyr Thr Phe
                 85                  90                  95

Gly Gly Gly Thr Lys Leu Glu Leu Lys Arg Ala Ala Ala
             100                 105

<210> SEQ ID NO 35
<211> LENGTH: 327
<212> TYPE: DNA
<213> ORGANISM: Artificial Sequence
<220> FEATURE:
<223> OTHER INFORMATION: MCU-1 scFv light chain

<400> SEQUENCE: 35

```
gatattgaac tgacccagag cccggcgatt atgagcgcga gcccgggcga acgcgtgacc      60
atgacctgca gcgcgagcag cagcattcgc tatatttatt ggtatcagca gaaaccgggc     120
agcagcccgc gcctgctgta tgataccagc aacgtggcgc gggcgtgcc gtttcgcttt      180 agcggcagcg gcagcggcac cagctatagc ctgaccatta accgcatgga agcggaagat     240
gcggcgacct attattgcca ggaatggagc ggctatccgt atacctttgg cggcggcacc     300
aaactggaac tgaaacgcgc ggcggcg                                         327
```

<210> SEQ ID NO 36
<211> LENGTH: 129
<212> TYPE: PRT
<213> ORGANISM: Artificial Sequence
<220> FEATURE:
<223> OTHER INFORMATION: EGFR scFv heavy chain

<400> SEQUENCE: 36

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Leu Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Ser Ser Ser Asn Cys Ala Lys Trp
            100                 105                 110

Pro Glu Tyr Phe Gln His Trp Gly Gln Gly Thr Leu Val Thr Val Ser
        115                 120                 125

Ser
```

<210> SEQ ID NO 37
<211> LENGTH: 387
<212> TYPE: DNA
<213> ORGANISM: Artificial Sequence
<220> FEATURE:
<223> OTHER INFORMATION: EGFR scFv heavy chain

<400> SEQUENCE: 37

```
caggtgcagc tggtgcagag cggcgcggaa gtgaaaaaac cgggcgaaag cctgaaaatt      60
agctgcaaag gcagcggcta tagctttacc agctattggc tggcgtgggt gcgccagatg     120
ccgggcaaag gcctggaata tatgggcctg atttatccgg gcgatagcga taccaaatat     180
agcccgagct ttcagggcca ggtgaccatt agcgtggata aaagcgtgag caccgcgtat     240
ctgcagtgga gcagcctgaa accgagcgat agcgcggtgt attttgcgc gcgccatgat     300 gtgggctatt gcagcagcag caactgcgcg aaatggccgg aatattttca gcattggggc     360
cagggcaccc tggtgaccgt gagcagc                                         387
```

<210> SEQ ID NO 38
<211> LENGTH: 111
<212> TYPE: PRT

<213> ORGANISM: Artificial Sequence
<220> FEATURE:
<223> OTHER INFORMATION: EGFR scFv light chain

<400> SEQUENCE: 38

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
                35                  40                  45

Ile Tyr Gly His Thr Asn Arg Pro Ala Gly Val Pro Asp Arg Phe Ser
        50                  55                  60

Gly Ser Lys Ser Gly Thr Ser Ala Ser Leu Ala Ile Ser Gly Phe Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu Gly
            100                 105                 110
```

<210> SEQ ID NO 39
<211> LENGTH: 333
<212> TYPE: DNA
<213> ORGANISM: Artificial Sequence
<220> FEATURE:
<223> OTHER INFORMATION: EGFR scFv light chain

<400> SEQUENCE: 39

```
cagagcgtgc tgacccagcc gccgagcgtg agcgcggcgc cgggccagaa agtgaccatt        60
agctgcagcg gcagcagcag caacattggc aacaactatg tgagctggta tcagcagctg       120
ccgggcaccg cgccgaaact gctgatttat ggccatacca accgcccggc gggcgtgccg       180
gatcgcttta gcggcagcaa aagcggcacc agcgcgagcc tggcgattag cggctttcgc       240
agcgaagatg aagcggatta ttattgcgcg gcgtgggatg atagcctgag cggctgggtg       300
tttggcggcg gcaccaaact gaccgtgctg ggc                                    333
```

<210> SEQ ID NO 40
<211> LENGTH: 227
<212> TYPE: PRT
<213> ORGANISM: Artificial Sequence
<220> FEATURE:
<223> OTHER INFORMATION: VEGFR scFv heavy chain

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
                35                  40                  45

Ala Gly Ile Thr Pro Ala Gly Gly Tyr Thr Tyr Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110
```

```
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His
225

<210> SEQ ID NO 41
<211> LENGTH: 681
<212> TYPE: DNA
<213> ORGANISM: Artificial Sequence
<220> FEATURE:
<223> OTHER INFORMATION: VEGFR scFv heavy chain

<400> SEQUENCE: 41
gaagtgcagc tggtggaaag cggcggcggc ctggtgcagc cgggcggcag cctgcgcctg      60
agctgcgcgg cgagcggctt taccattagc gattattgga ttcattgggt cgcgcaggcg     120
ccgggcaaag gcctggaatg ggtggcgggc attaccccgg cgggcggcta taccattat      180 gcggatagcg tgaaaggccg ctttaccatt agcgcggata ccagcaaaaa caccgcgtat     240
ctgcagatga acagcctgcg cgcggaagat accgcggtgt attattgcgc gcgctttgtg     300 tttttttctgc cgtatgcgat ggattattgg ggccagggca ccctggtgac cgtgagcagc     360
gcgagcacca aggcccgag cgtgtttccg ctggcgccga gcagcaaaag caccagcggc     420
ggcaccgcgg cgctgggctg cctggtgaaa gattattttc cggaaccggt gaccgtgagc     480
tggaacagcg gcgcgctgac cagcggcgtg cataccttc cggcggtgct gcagagcagc      540
ggcctgtata gcctgagcag cgtggtgacc gtgccgagca gcagcctggg cacccagacc     600
tatatttgca acgtgaacca taaaccgagc aacaccaaag tggataaaaa agtggaaccg     660
aaaagctgcg ataaaaccca t                                                681

<210> SEQ ID NO 42
<211> LENGTH: 214
<212> TYPE: PRT
<213> ORGANISM: Artificial Sequence
<220> FEATURE:
<223> OTHER INFORMATION: VEGFR scFv light chain

<400> SEQUENCE: 42

Asp Ile Gln Met Thr Gln Ser Pro Ser Ser Leu Ser Ala Ser Val Gly
1               5                   10                  15
Asp Arg Val Thr Thr Thr Cys Arg Ala Ser Gln Asp Val Ser Thr Ala
            20                  25                  30
Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
     50                  55                  60

Ser Gly Ser Gly Thr Asp Phe Thr Leu Thr Ile Ser Ser Leu Gln Pro
 65              70                  75                      80

Glu Asp Phe Ala Thr Tyr Tyr Cys Gln Gln Ser Tyr Thr Thr Pro Pro
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 43
<211> LENGTH: 642
<212> TYPE: DNA
<213> ORGANISM: Artificial Sequence
<220> FEATURE:
<223> OTHER INFORMATION: VEGFR scFv light chain

<400> SEQUENCE: 43
gatattcaga tgacccagag cccgagcagc ctgagcgcga gcgtgggcga tcgcgtgacc      60
accacctgcc gcgcgagcca ggatgtgagc accgcggtgg cgtggtatca gcagaaaccg     120
ggcaaagcgc cgaaactgct gatttatagc gcgagctttc tgtatagcgg cgtgccgagc     180
cgctttagcg gcagcggcag cggcaccgat tttaccctga ccattagcag cctgcagccg     240
gaagattttg cgacctatta ttgccagcag agctatacca ccccgccgac ctttggccag     300
ggcaccaaag tggaaattaa acgcaccgtg gcggcgccga gcgtgtttat ttttccgccg     360
agcgatgaac agctgaaaag cggcaccgcg agcgtggtgt gcctgctgaa caactttat      420 ccgcgcgaag cgaaagtgca gtggaaagtg gataacgcgc tgcagagcgg caacagccag     480
gaaagcgtga ccgaacagga tagcaaagat agcacctata gcctgagcag cacccctgacc    540 ctgagcaaag cggattatga aaaacataaa gtgtatgcgt gcgaagtgac ccatcagggc     600
ctgagcagcc cggtgaccaa aagctttaac cgcggcgaat gc                         642
```